US012396776B2

(12) United States Patent
Davidner et al.

(10) Patent No.: US 12,396,776 B2
(45) Date of Patent: Aug. 26, 2025

(54) ORTHOPEDIC SURGERY SYSTEMS AND DEVICES FOR IMPACTING IMPLEMENTS IN BONES

(71) Applicant: OrthoIQ, LLC, Claremont, CA (US)

(72) Inventors: Alan Aaron Davidner, Claremont, CA (US); Anthony La Rosa, Rockaway, NJ (US); Philip Ormond Merritt, La Canada, CA (US); Michael Nogler, Oberperfuss Tirol (AT); José-Luis Moctezuma De La Berrera, Freiburg im Breisgau (DE)

(73) Assignee: OrthoIQ, LLC, Claremont, CA (US)

( * ) Notice: Subject to any disclaimer, the term of this patent is extended or adjusted under 35 U.S.C. 154(b) by 0 days.

(21) Appl. No.: 18/948,017

(22) Filed: Nov. 14, 2024

(65) Prior Publication Data
US 2025/0152224 A1    May 15, 2025

Related U.S. Application Data

(60) Provisional application No. 63/663,824, filed on Jun. 25, 2024, provisional application No. 63/599,219, filed on Nov. 15, 2023.

(51) Int. Cl.
*A61B 17/92* (2006.01)
*A61B 17/00* (2006.01)
(52) U.S. Cl.
CPC .... *A61B 17/92* (2013.01); *A61B 2017/00137* (2013.01); *A61B 2017/00398* (2013.01);
(Continued)

(58) Field of Classification Search
CPC .............. A61B 17/92; A61B 2017/927; A61B 2017/922; A61B 17/1659; A61B 17/164;
(Continued)

(56) References Cited

U.S. PATENT DOCUMENTS 1,860,826 A * 5/1932 Tschudi ................. B25D 11/10
173/205
3,127,941 A * 4/1964 Sieber .................. B25D 11/068
173/98

(Continued)

OTHER PUBLICATIONS

International Search Report and Written Opinion mailed Feb. 14, 2025 re PCT/US2024/056010 (8 pages).

*Primary Examiner* — David W Bates
(74) *Attorney, Agent, or Firm* — Aurora Consulting LLC

(57) ABSTRACT

Systems and devices may include a motor operatively coupled to a driveshaft configured to be driven in a first direction in a first mode for impaction and a second direction in a second mode for retraction. Systems and devices may include an anvil configured to be operatively coupled to an implement. Systems and devices may include an impaction cam operatively coupled to the driveshaft, wherein: the impaction cam, when in an impaction position, is configured to strike the anvil when driven by the driveshaft in the first direction to drive the anvil in an impaction direction. Systems and devices may include a retractor configured to be driven by the retraction cam in the second direction, wherein the retractor is configured to strike the anvil to drive the anvil in a retraction direction.

20 Claims, 31 Drawing Sheets

(52) U.S. Cl.
CPC ............... *A61B 2017/00477* (2013.01); *A61B 2017/00734* (2013.01); *A61B 2017/925* (2013.01)

(58) Field of Classification Search
CPC ................. B25D 11/068; B25D 11/066; A61F 2002/4681; A61F 2002/4619
See application file for complete search history.

(56) References Cited

U.S. PATENT DOCUMENTS

| | | | | |
|---|---|---|---|---|
| 4,909,419 | A * | 3/1990 | Yamada | B25C 1/045 227/1 |
| 5,025,869 | A * | 6/1991 | Terunuma | B25D 11/04 173/98 |
| 5,057,112 | A * | 10/1991 | Sherman | A61B 17/1659 606/86 R |
| 5,485,887 | A * | 1/1996 | Mandanis | B25D 17/06 173/91 |
| 6,959,478 | B2 * | 11/2005 | Chen | B25D 17/24 29/451 |
| 7,588,093 | B2 * | 9/2009 | Grand | B25B 21/026 173/29 |
| 7,879,043 | B2 | 2/2011 | Meneghini et al. | |
| 7,963,430 | B2 * | 6/2011 | Fukinuki | B25C 1/06 173/205 |
| 8,236,005 | B2 | 8/2012 | Meneghini et al. | |
| 8,256,527 | B2 * | 9/2012 | Wu | B25C 1/188 173/217 |
| 8,297,373 | B2 * | 10/2012 | Elger | B25C 5/15 173/100 |
| 8,348,120 | B2 * | 1/2013 | Wei | B25F 5/02 81/177.5 |
| 8,485,276 | B2 * | 7/2013 | Wei | B25D 11/068 173/217 |
| 8,678,262 | B2 * | 3/2014 | Zhou | B25C 1/06 279/57 |
| 8,696,756 | B2 | 4/2014 | Stein et al. | |
| 8,783,378 | B2 * | 7/2014 | Zhou | B25D 11/068 173/91 |
| 8,978,951 | B2 * | 3/2015 | Wei | B25D 11/068 227/147 |
| 9,931,151 | B2 | 4/2018 | Donald et al. | |
| 10,149,711 | B2 * | 12/2018 | Bittenson | A61B 17/92 |
| 10,245,162 | B2 * | 4/2019 | Behzadi | A61F 2/4609 |
| 10,406,664 | B2 * | 9/2019 | Zhang | B25C 1/047 |
| 11,696,770 | B2 | 7/2023 | Pedicini | |
| 11,766,381 | B2 | 9/2023 | Marton et al. | |
| 12,186,003 | B2 * | 1/2025 | Wallace | A61B 17/92 |
| 2009/0045241 | A1 * | 2/2009 | Fukinuki | B25C 1/06 227/131 |
| 2011/0094764 | A1 * | 4/2011 | Wei | F21V 33/0084 173/122 |
| 2011/0100662 | A1 * | 5/2011 | Wei | B25F 5/02 173/90 |
| 2012/0232562 | A1 * | 9/2012 | Mani | A61F 2/4612 606/100 |
| 2013/0204264 | A1 * | 8/2013 | Mani | A61F 2/4612 623/22.11 |
| 2014/0262398 | A1 * | 9/2014 | Gehret | B25D 11/068 173/94 |
| 2018/0055518 | A1 | 3/2018 | Pedicini | |
| 2018/0055553 | A1 * | 3/2018 | Pedicini | A61B 17/92 |
| 2019/0216521 | A1 * | 7/2019 | Chhatrala | A61B 17/921 |
| 2022/0142693 | A1 | 5/2022 | Slocum et al. | |
| 2022/0151641 | A1 * | 5/2022 | Lashure | A61B 17/92 |
| 2022/0226033 | A1 * | 7/2022 | Slocum | A61B 17/92 |
| 2022/0233225 | A1 | 7/2022 | Pedicini et al. | |
| 2022/0240946 | A1 | 8/2022 | Slocum et al. | |
| 2022/0240998 | A1 | 8/2022 | Slocum | |
| 2022/0273317 | A1 * | 9/2022 | Levy | A61B 17/92 |
| 2022/0323134 | A1 * | 10/2022 | Lyon | A61B 17/92 |
| 2022/0339769 | A1 * | 10/2022 | Beer | B25D 11/10 |
| 2024/0024012 | A1 | 1/2024 | Dittrich et al. | |

\* cited by examiner

ORTHOPEDIC SURGERY SYSTEMS AND DEVICES FOR IMPACTING IMPLEMENTS IN BONES

CROSS-REFERENCE TO RELATED APPLICATIONS

This application claims the priority benefit of U.S. Provisional Patent Application Ser. No. 63/599,219, filed Nov. 15, 2023, and U.S. Provisional Patent Application Ser. No. 63/663,824, filed Jun. 25, 2024, the contents of each of which are herein incorporated by reference in their entirety.

INCORPORATION BY REFERENCE

All publications and patent applications mentioned in this specification are herein incorporated by reference in their entirety, as if each individual publication or patent application was specifically and individually indicated to be incorporated by reference in its entirety.

TECHNICAL FIELD

This disclosure relates generally to the field of orthopedic surgery (e.g., reconstructive surgery of the hip, knee, shoulder, and ankle), the repair of bone fractures, and more specifically, to the preparation of the bone for placement of implant components and insertion of fixation devices. Described herein are systems and methods for easily, safely, and effectively using powered instrument systems for impacting implantable devices into bone.

BACKGROUND

The frequency of Total Hip Arthroplasty (THA) procedures is expected to grow to 635,000 procedures by the year 2030. The procedure relieves pain and improves motion with little to no down time. THA is usually a safe and effective procedure with few complications. When complications do arise, they may require revision hip surgery. Revision hip surgery can cost upwards of $73,500, may result in long hospital stays, and serious co-morbidities are possible. Complications occur at a rate of 3.5% and include instability and/or dislocation and, especially, peri-prosthetic femur fractures (i.e., fractures that occur around and, as a result of, the insertion of the broach, implant, or stem).

Additionally, the frequency of Total Shoulder Arthroplasty (TSA) procedures is expected to grow to 173,500 procedures by the year 2025. Like THA, TSA has equivalent complications. When complications arise, dislocation and periprosthetic fractures may also occur.

Moreover, surgeons suffer stress on their wrist, arm, shoulder, and back when employing manual hammers or heavy unbalanced impactors during orthopedic surgeries. The stress can lead to workman compensation issues, rehabilitation time off, and a potential reduction in working longevity. The population of orthopedic surgeons is increasing at a 1.5% annual rate while the number of hip surgeries are increasing at a 4.5% annual rate. Surgeons are therefore forced to do more surgeries, thus leaving them even more prone to stress related injuries.

SUMMARY

In some aspects, the techniques described herein relate to an orthopedic impactor system, including: a motor operatively coupled to a driveshaft, wherein the driveshaft is configured to be driven in a first direction in a first mode for impaction and a second direction in a second mode for retraction; an anvil configured to be operatively coupled to a broach or a stem; an impaction cam operatively coupled to the driveshaft, wherein: the impaction cam, when in an impaction position, is configured to strike the anvil when driven by the driveshaft in the first direction to drive the anvil in an impaction direction, the impaction cam is configured to be retarded when a minimum force is sustained by the anvil, when retarded, the impaction cam is configured to be forced out of contact with the anvil in a first axial direction along a longitudinal axis of the driveshaft, and the impaction cam is configured to be forced back into the impaction position in a second axial direction when the impaction cam rotates past the anvil; a retraction cam operatively coupled the driveshaft, wherein the retraction cam is configured to be driven to spin by the driveshaft in the second direction; and a retractor configured to be driven by the retraction cam in the second direction, wherein the retractor is configured to strike the anvil to drive the anvil in a retraction direction, In some aspects, the techniques described herein relate to an orthopedic impactor system, including: a motor operatively coupled to a driveshaft, wherein the driveshaft is configured to be driven in a first direction and a second direction; an anvil configured to be operatively coupled to a broach or a stem; and an impaction cam operatively coupled to the driveshaft, wherein: the impaction cam is configured to strike the anvil when driven by the driveshaft to drive the anvil in an impaction direction, impaction cam is configured to be retarded when a minimum force is sustained by the anvil, and retarding the impaction cam is configured to force the impaction cam out of contact with the anvil in a first axial direction along a longitudinal axis of the driveshaft.

In some aspects, the techniques described herein relate to a method of using an impactor on a prepared bone including: activating an impactor for impaction using high-frequency, low force impacts, wherein impaction includes: driving a driveshaft in a first direction to drive an impaction cam operatively coupled to the driveshaft, impacting an anvil with the impaction cam such that the anvil is driven in an impaction direction, when a minimum force is sustained by the anvil, disengaging the impaction cam from the anvil by allowing retardation of the impaction cam with respect to the driveshaft and translating the impaction cam in a second axial direction along a longitudinal axis of the driveshaft until the impaction cam is out of contact with the anvil, and forcing the impaction cam back in a first axial direction to an impaction position for a subsequent impact; broaching a canal of the bone; and installing a stem.

BRIEF DESCRIPTION OF THE DRAWINGS

The foregoing is a summary, and thus, necessarily limited in detail. The above-mentioned aspects, as well as other aspects, features, and advantages of the present technology are described below in connection with various embodiments, with reference made to the accompanying drawings.

Figure 1A:
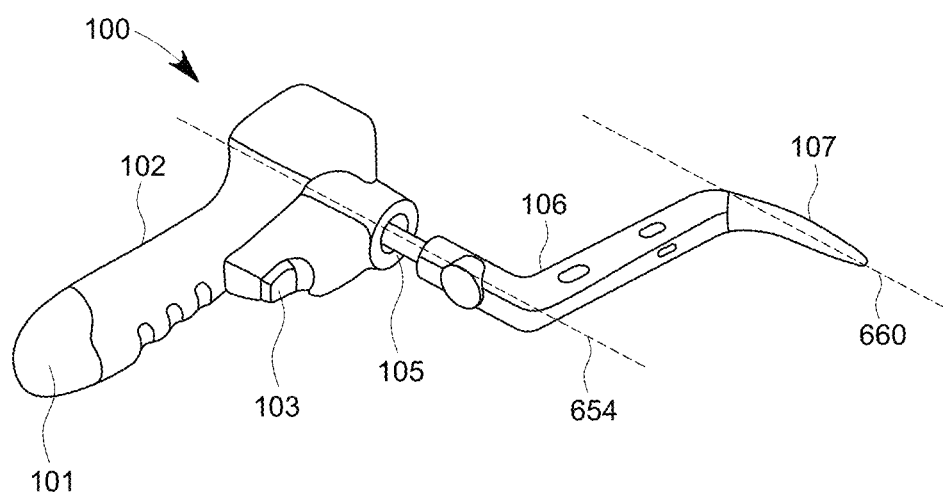
FIG. 1A illustrates an embodiment of an automatic impactor with a double offset implement handle.

The illustrated embodiments are merely examples and are not intended to limit the disclosure. The schematics are drawn to illustrate features and concepts and are not necessarily drawn to scale.

DETAILED DESCRIPTION

The foregoing is a summary, and thus, necessarily limited in detail. The above-mentioned aspects, as well as other aspects, features, and advantages of the present technology will now be described in connection with various embodiments. The inclusion of the following embodiments is not intended to limit the disclosure to these embodiments, but rather to enable any person skilled in the art to make and use the claimed subject matter. Other embodiments may be utilized, and modifications may be made without departing from the spirit or scope of the subject matter presented herein. Aspects of the disclosure, as described and illustrated herein, can be arranged, combined, modified, and designed in a variety of different formulations, all of which are explicitly contemplated and form part of this disclosure.

Surgeons struggle with controlling the broaching process, for example, during the installation of implants into bone (e.g., the femur, humerus, and tibia). A small variance between swings of a hammer can create a large change in impact force between the swings. Several factors may increase difficulty during the broaching process, for example, the large change in force of manual mallets resulting from little variance in swing or the large amplitude motors of impactors known in the art are often do not include options to control force. As a means of facilitating the broaching process, broach handles are utilized. These are implements that connect impactors to broaches and implants, and function to transmit force. Implement handles with strike plates also function to transmit force from a manual hammer. These implement handles may be made of a large mass of stainless steel (e.g., approximately 9 N (2 lbs. of force)) to facilitate stiffness. A particular stiffness may function to transmit energy more effectively. Unfortunately, a large mass of stainless steel also absorbs some of the energy, therefore, creating wasted energy. Wasted energy causes the surgeon to strike the broach handle with more force, further increasing the stress placed on the wrist, arm, shoulder, and/or back. Finally, the surgeon works to overcome the perpendicular frictional force as the broach or implant is advanced into the bone canal. The frictional force is caused by the interaction of the broach or implant when compressing the cancellus bone.

The systems and methods described herein solve the above problems by providing a surgeon with a way to control the force applied with an ergonomic and balanced impactor. Described herein are technical solutions for preventing bone fractures, providing atraumatic ways of managing already fractured bones, and/or alleviating fatigue and stress on surgeons. Described herein are technical solutions for applying force to orthopedic tools and/or orthopedic implants that reduces the likelihood of fractures and/or improves implant seating.

Orthopedic tool may be used herein to describe broaches, reamers, rasps, osteotomes, files, bone taps, awls, curettes, trial components, and the like.

Orthopedic implant may be used herein to describe stems (e.g., femoral stems, tibial stems, humeral stems, radial stems, ulnar stems, and the like), orthopedic nails, and the like. Implement may be used herein to describe the aforementioned tools and implants.

By applying the force with higher frequency and smaller amplitude than a standard mallet or currently available automatic impactor, the surgeon has a further measure of control. Moreover, by using vibration perpendicularly applied to an implement, the amount of force applied can be reduced by, for example, as much as about 20% to about 60%; about 25% to about 55%; about 30% to about 50%; etc. A high frequency vibration overlaying the impaction contributes to diminishing or eliminating the stick-slip effect that otherwise is present when applying a cyclical low frequency impaction where the advancement of the surgical tool stops after an impaction. The high frequency vibration induces micromotion at the interface between the tissue and the surgical tool thus avoiding the transition of the friction forces to a higher static friction force when the motion stops as opposed to lower gliding friction that is present when there is a relative movement between the surface of the surgical instrument and the surrounding tissue. The stick-slip phenomenon has its principles in the discontinuity between static and kinetic friction. More precisely, the stick-slip effect occurs if the static coefficient of friction is higher than the dynamic coefficient of friction as well and the slide velocity is slow. In this case, overlaying the small amplitude, high frequency vibration maintains the surgical tool in relative motion and thus not falling into the higher static friction envelope. Said another way, once inertia and static friction are overcome, it is more efficient to keep an orthopedic tool and/or orthopedic implant (i.e., implement 107) in motion, overcoming kinetic friction. These technical solutions provide significant advantages. For example, less energy is used to overcome the higher static friction, since the implement 107 is in a gliding state. For example, control is enhanced over the impaction process due to reduced impaction force used. The precision of the surgical preparation is enhanced due to the substantially continuous gliding impaction process.

Implementation of impaction overlayed with a high-frequency, low-amplitude vibratory motion can be achieved in several ways as described herein. There exist many beneficial applications of this approach. For example, surgeons struggle with removing femoral stems and tibial and femur nails during an orthopedic revision process, as removing a bone nail can be a difficult process. In addition, tooth extraction or removing a medical implement may be difficult. The systems and methods described herein solve the above problems with the use of vibration singularly or in combination with a mallet, forceps, or an impactor. The reversing mechanism of the impactor also provides sufficient force for extraction in addition to the aforementioned capabilities.

Nailing fractured bones, such as shoulder, arm, femur, tibia, etc., can be problematic because of the difficulty in controlling manual hammers. Installing nails with too much or too little force can create unsatisfactory repairs. The systems and methods described herein solve the above problems by employing the impactor described herein to control force and, in some embodiments, utilize vibration as an aid.

Another use case may be animals. For example, large breed dogs such as Great Danes, Saint Bernard, Labrador Retriever, and German Shepherds can suffer from hip dysplasia, a genetic disease. Small dogs may have bone growth plate fractures during development. Small and miniature horses also can be afflicted with hip problems. Dog owners may employ veterinary surgeons to replace the hip joints or repair growth plates with nails. Implants and nails used in these cases are often small. Therefore, pediatric or small adult implants or small nails are utilized. Veterinary hammers are utilized to fixate these implements. Even though the hammers are smaller than adult versions, small hammers still present control problems.

The systems and methods described herein solve the above problems by employing the impactor described herein. Thus, controlling the force and/or utilizing vibration as an aid in solving this problem.

During orthopedic surgery for implants and repair, a variety of hammers are often employed for chiseling (including an osteotome), gouging, splitting, tampering, and/or slicing. Multiple hammers can be utilized with some dubious results. Using multiple hammers may cause the surgeon to change out several hammers during a surgery. For example, a myriad of hammers may include: Cloward, Narrow Hip, Heath, He-Man, Herzog, Repercussion Free Mallet and including, but not limited to, various weights of hammers. These weights for example can be about 4.5 N (1 lb. of force), about 9 N (2 lbs. of force), about (2.5 lbs. of force), about 13.5 N (3 lbs. of force), etc.

The systems and methods described herein solve the above problems by employing the impactor described herein. The impactors described herein may be scaled appropriately for different applications and uses. Solutions described herein eliminate stocking, sterilizing, and providing a myriad of hammers during surgery. Controlling the force and utilizing vibration to reduce the force used and/or a smaller version help solve this technical problem.

The installation of cages in spinal fusion includes similar problems found in orthopedic implant surgery. Whether it is lateral, posterior, or an anterior approach to the surgery, a large force is used. With the force used, it may be awkward to hammer the cage to fixation.

The systems and methods described herein solve the above problems by employing the impactor embodiments described herein. A large force may not be used because of the use of vibration and a smaller force from the impactor. Further, an offset handle as described herein may provide easier spinal vertebral access to allow for fixation of the spinal cage.

Alveolar bone resorption during tooth extraction can cause trauma and bleeding. The systems and methods described herein solve the above problems by employing a smaller version of the impactor described herein. By utilizing vibration and/or a smaller force, the tooth extraction can be less traumatic. Utilizing impactors described herein may replace additional surgical devices that are conventionally used, for example, elevators, peristomes, and forceps.

There presently exists commercial and residential applications in which hammers, and bulky impactors are not practical or ergonomic. These problems include, but are not limited to, hammering nails in confined spaces, breaking up wood knots, making steel letters more pliable, or in agriculture, where large impact drivers are used to drive metal tipped pensile harrow points into the ground to break up the soil.

The systems and methods described herein solve the above problems by employing a straight or offset version of an implement handle that is connected to the impactor. The handle is lighter but stiff enough to deploy the force. Compared to a standard chisel or implement, the work to use the impactor and connected implement is not as tiring.

The systems and devices described herein function to broach bones (e.g., femurs and humeri) and create sufficient space for the installation of an implant or stem. In some embodiments, the systems and devices function to install a stem and/or acetabular component. In some embodiments, the systems and devices employ vibration to aid in broaching and/or installation of a stem and/or acetabular component. In some embodiments, the systems and devices provide light and/or a camera system to view and/or memorialize the cortical rim area or any bone area. In some embodiments, a lightweight and/or rigid implement handle is employed. The systems and devices are used for orthopedic hip and shoulder implant surgery, but can additionally, or alternatively, be used for any suitable applications, clinical or otherwise as described herein. The systems and devices can be configured and/or adapted to function for any suitable spine, trauma, sports medicine surgery, reconstructive surgery, ENT, veterinary surgery, dental surgery, and commercial and residential uses.

Figure 1B:
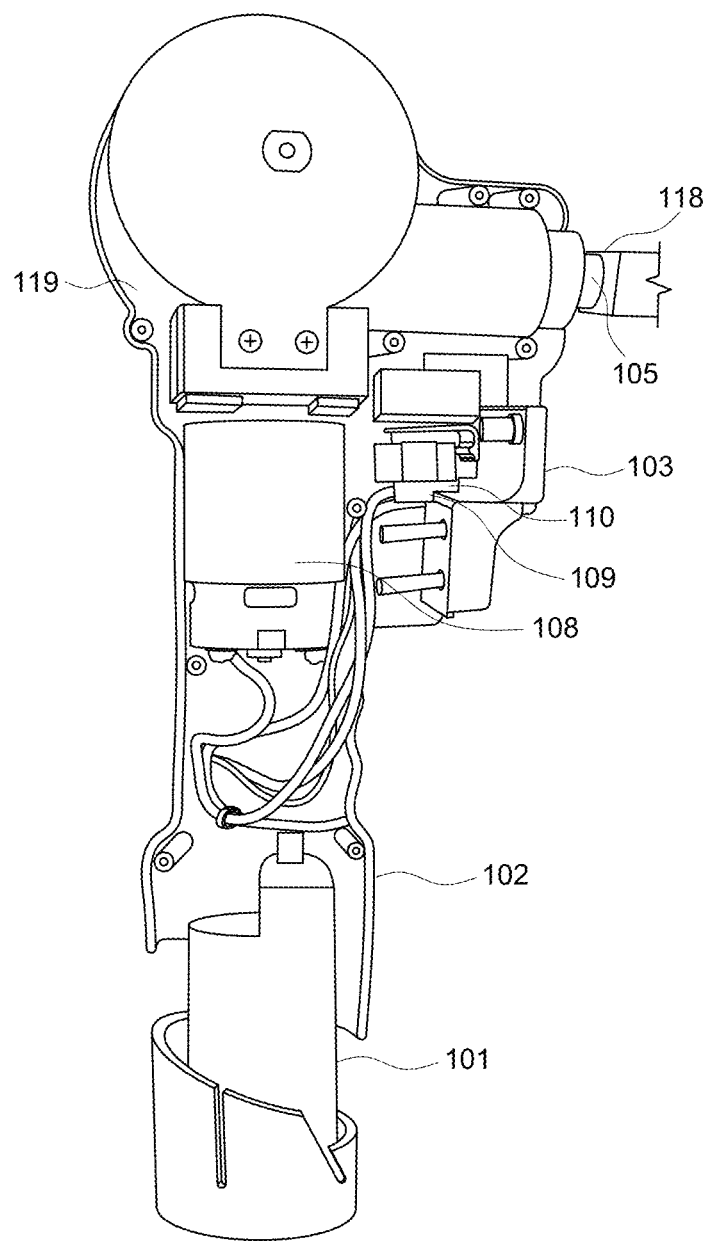
FIG. 1B illustrates the internal components in a housing of the automatic impactor of FIG. 1A.

Now referring to FIGS. 1A-1B, in some embodiments, an automatic impactor 100 is shown with a double offset implement handle 106 and implement 107. As shown in FIGS. 1A, a longitudinal axis 654 of the implement handle 106 is approximately parallel to a longitudinal axis 660 of the implement 107 but is not colinear with the longitudinal axis 660 of the implement 107. The implement handle 106 serves to connect and transmit motive force from the impactor to the implement 107. The implement handle 106 can also serve to transmit perpendicular or, in some cases, in-line vibration to the implement (e.g., broach or stem). The impactor 100 may include a battery 101, a housing 102, a control input 103, variable vibration trigger 104, a connection mechanism 105 for coupling to an implement handle 106 and implement 107. In some embodiments, the battery 101 may be operatively coupled such that the battery 101 is quickly coupled and decoupled to facilitate battery 101 changes and/or charging. As shown in FIG. 1B, the housing 102 may at least partially cover and/or hold a plurality of components. The plurality of components may include an electric motor 108, a gear train, an impaction cam 114 (shown in FIGS. 6A-6D), a conical spring 113 (shown in FIGS. 6B-6C), an anvil 118, one or more batteries 101, an electronic driver 109, and other electronic control elements (e.g., an H-Bridge, a microcontroller, a polyfused, etc.). The electronic driver 109 may be used for speed control of the motor 108, DC to AC inversion, and/or control of motor direction. As shown in FIG. 6B, the gear train may include a ring gear 117a driven by a conical pinion 117b. Other gear trains or alternatives contemplated herein include chain and sprocket, belt and pulley, etc. In some embodiments, a hermetic chamber 119 (shown in FIG. 1B) may provide humidity and at least partial temperature insulation for the motor 108 and electronic components. The electric components could be integrally formed in, or fixed to, a single electronic board (e.g., a printed circuit board).

Figure 6A:
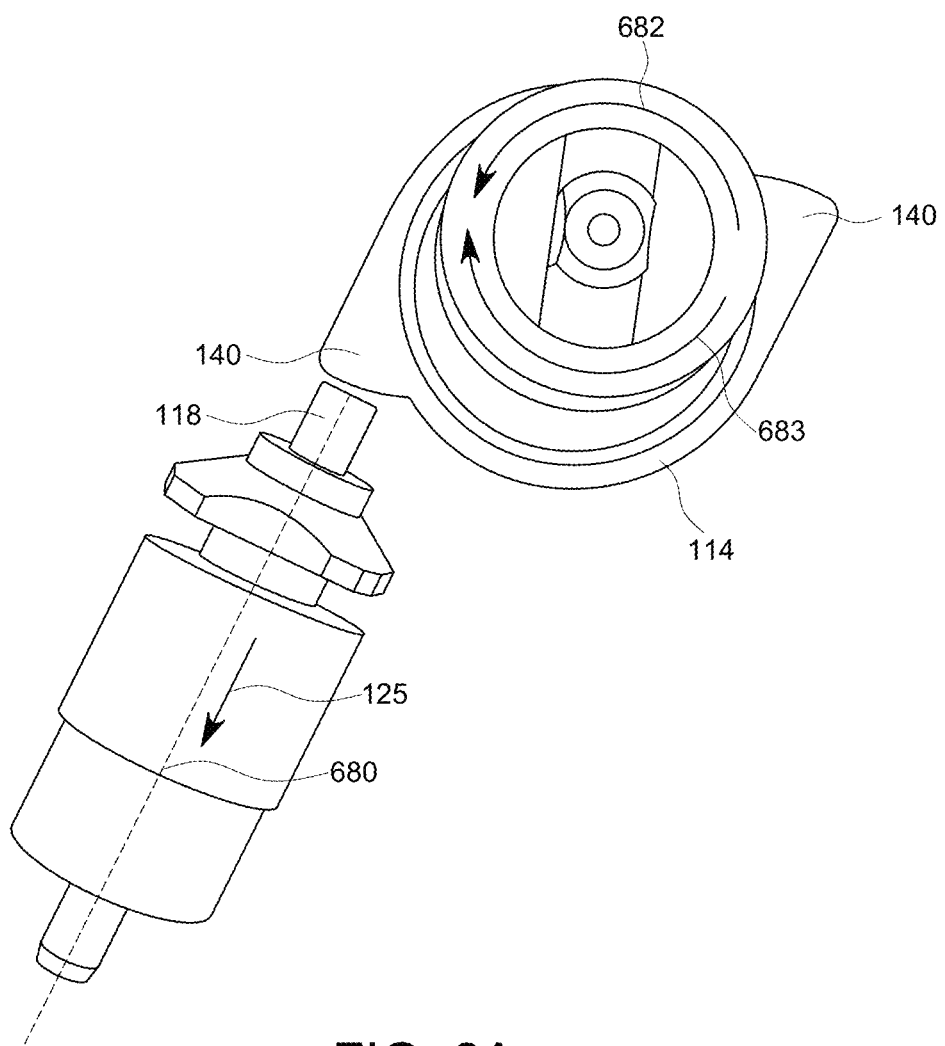
FIG. 6A illustrates an embodiment of a cam assembly that generates a motive impact force on an anvil.
Figure 6B:
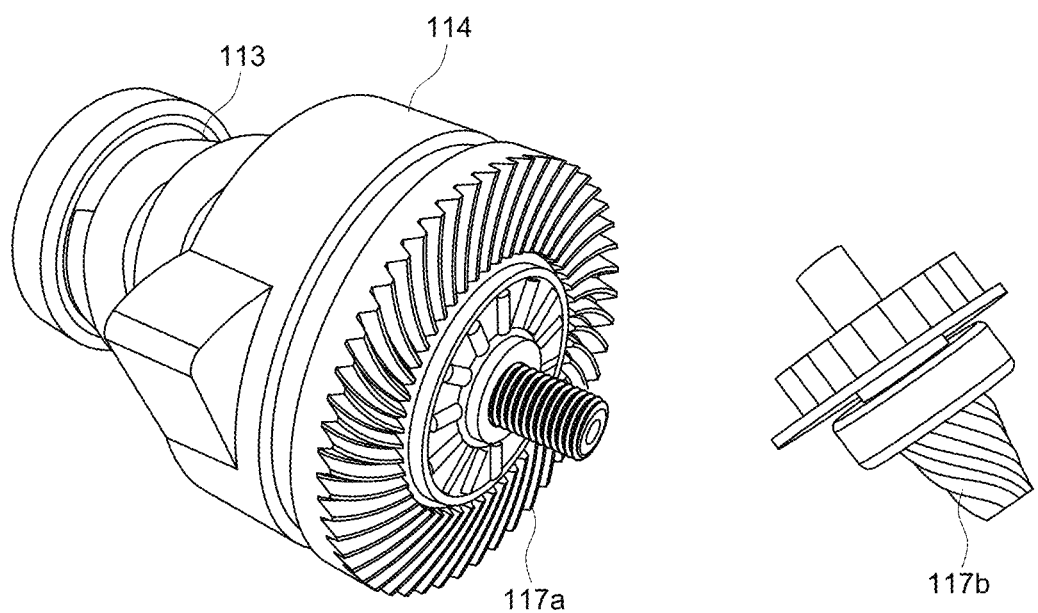
FIG. 6B illustrates a perspective view of a cam assembly with an attached gear.
Figure 7:
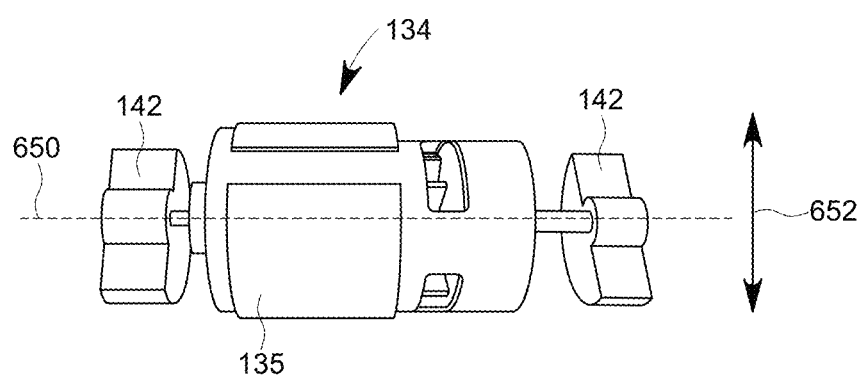
FIG. 7 illustrates an embodiment of a vibratory mechanism.

As shown in FIG. 1A, impactor 100 may provide controlled percussive impacts in a direction (i.e., impaction direction or retraction direction) along a longitudinal axis 654 (parallel to the longitudinal axis 680 of the anvil 118 shown in FIG. 6A) of the implement handle 106. The longitudinal axis 654 of the impactor 100 is approximately parallel to a longitudinal axis 660 of the implement 107. As such, the percussive impacts may be transferred via the implement handle 106 into the implement 107 along the longitudinal axis 660 of the implement 107. The percussive impacts can be controlled by using a control input 103, for example a variable force trigger or a variable position trigger. For example, the control input 103, when pressed, may complete an electrical circuit and transmit current from the battery 101, or another power source, to the motor 108. The harder the trigger is pressed or the further the trigger is moved (i.e., the more the trigger is depressed), the more current flows, allowing for finer control over the frequency of impactor 100. The control input 103 may control frequency proportionally, for example, a trigger depressed 25% results in an impact frequency that is 25% of the maximum frequency. The control input 103 may perform in discrete steps, for example, position thresholds for low, medium, and high may be used for discrete control of the impact frequency. The control input 103 may vary impact frequency, for example, from about 0 Hz to about 35 Hz or more. In some embodiments, the frequency range is from about 0 Hz to about 25 Hz. In some embodiments, the frequency range is from about 0 Hz to about 10 Hz; about 0 Hz to about 15 Hz; or about 0 Hz to about 20 Hz. The impactor 100 may transmit wireless communication to the wireless communication electronics of the vibratory assembly 130, as shown in FIG. 3B, in the implement handle 106. The wireless communication between the control input 103 and the wireless electronics 131 serves to attenuate the frequency of the vibrations of the vibratory assembly 130, as shown in FIG. 7. In some embodiments, the signal transmitted to the vibratory assembly 130 may include an activation signal. For example, when the control input 103 is pressed and the impactor is active, a signal to activate the vibratory assembly 130 may be transmitted to the vibratory assembly 130 to vibrate at a predefined frequency or in a predefined frequency range. Otherwise, the vibratory assembly 130 may not be active. In some embodiments, the frequency of vibrations produced by the vibratory assembly 130 may be controlled by the control input 103. For example, positional measurement or current measurement based on control input 103 position may be used to control the frequency of the vibratory assembly 130. Further, the frequency of the vibratory assembly 130 may be increased or decreased as the control input 103 is pressed harder (i.e., pressure is increased on control input 103). In accomplishing wireless transmission to the vibratory assembly 130, the impactor 100 may include wireless communication components (e.g., a transmitter, a transceiver, a microcontroller, etc.). The vibration frequency from the vibration motor 135 can vary from about 0 Hz to about 100 Hz or more. In some embodiments, the vibration frequency is from about 0 Hz to about 75 Hz with the vibration applied in a direction 652 (shown in FIG. 7) perpendicular to the implement (i.e., perpendicular to the longitudinal axis 660 of the implement 107). Although in some embodiments, the frequency range can range from about 0 Hz to about 50 Hz; about 0 Hz to about 35 Hz; or about 0 Hz to about 125 Hz. The vibrations could also be applied perpendicular and/or laterally. The connection mechanism 105 is configured to provide two or more positions of implement handle 106 for ergonomic insertion in the bone (e.g., femoral, humeri, etc.) canal or for work on any kind of bone. Therefore, in some embodiments, the implement handle 106 (or implement handle 129 shown in FIG. 4B) can be rotated relative to the impactor 100 in about 70 degree increments to about 110 degree increments; about 80 degree increments to about 100 degree increments; about 85 degree increments to about 95 degree increments; etc. In other embodiments, the implement handle 106 can be rotated in increments of about 5 degrees to about 45 degrees; about 45 degrees to about 120 degrees, about 120 degrees to about 180 degrees, about 120 degrees, about 180 degrees, or any degree amounts therebetween. The implement handle 106 (or implement handle 129 shown in FIG. 4B) is connected to the impactor and implement 107. The implement handle 106 (or implement handle 129 shown in FIG. 4B) serves to transmit the impact force to the implement. The implement handle 106 (or implement handle 129 shown in FIG. 4B) serves to transmit vibrations to the stem and broach.

Figure 2A:
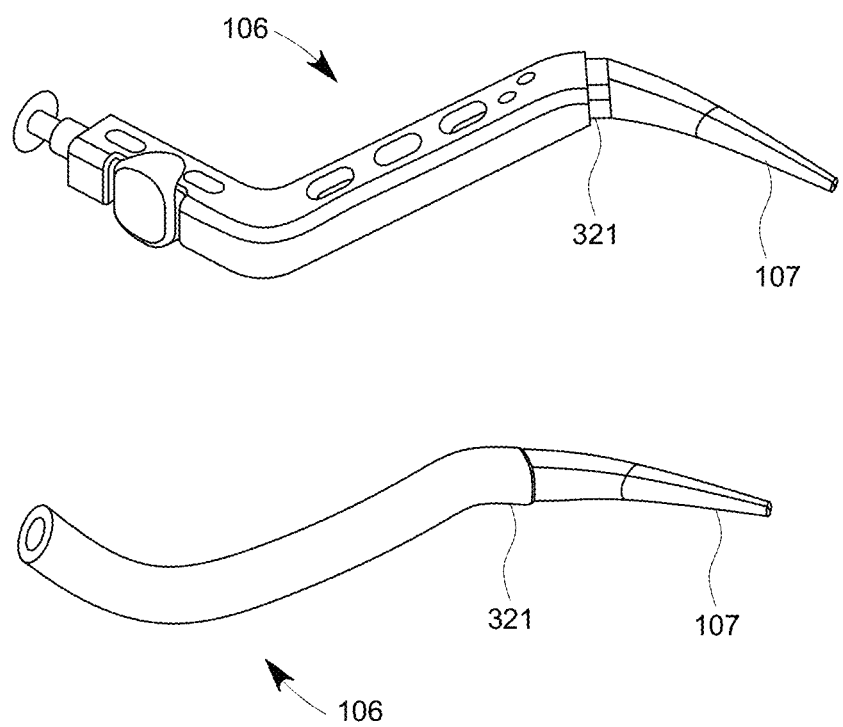
FIG. 2A illustrates a perspective view of an embodiment of an automatic impactor with a double offset implement handle.
Figure 2B:
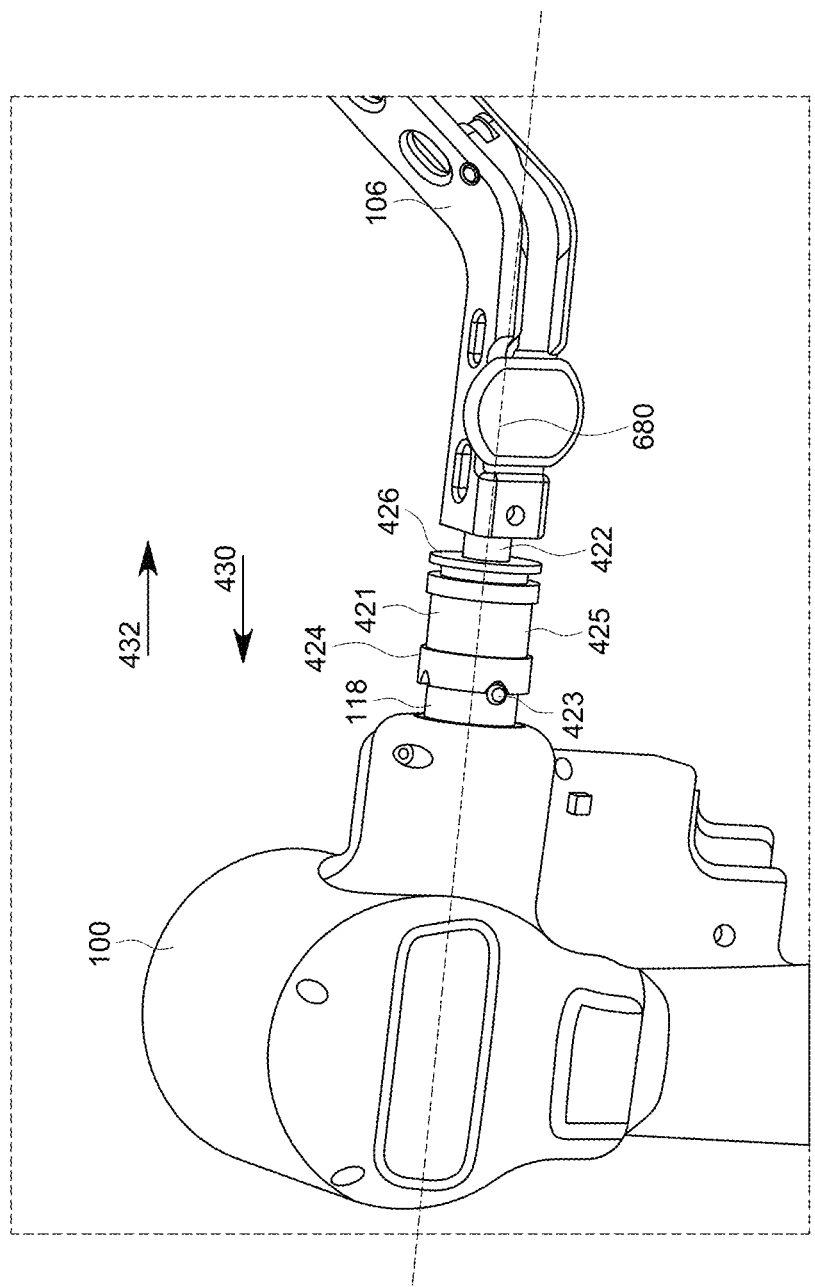
FIG. 2B illustrates a connection mechanism of an embodiment of an automatic impactor.

In FIG. 2A, an embodiment of a double offset implement handle 106 is shown in a rectangular and tubular configuration. It is contemplated herein that implement handles 106 (129 shown in FIG. 4B) may be rectangular (shown), tubular (shown), or any other cross-sectional shape with a moment of inertia that provides a desired amount of rigidity. A connection mechanism 321 can connect implement 107 to the implement handle 106. For example, a connection mechanism may be coupled to the implement handle 106 using a coupling element. Non-limiting examples of coupling elements may include an over-center toggle latch, a roller lock, a flat face lock, a quick-release coupling (e.g., a push button, twist lock, a collar and ball-detent, etc.), a bayonet coupling, or any other appropriate connection or coupling known in the art. FIG. 2B illustrates a connection mechanism 421 that may be used for connecting the implement handle 106 to the impactor 100 or the implement handle to a implement 107. The connection mechanism 421 defines an aperture 426 that may receive an attachment portion 422 of the implement handle 106 complementary to the defined aperture 426. The connection mechanism 421 may lock the attachment portion 422 to the impactor 100 when the collar 425 slides in direction 432 distally away from the impactor 100. The collar 425 may be biased toward direction 432, for example, using an operative coupling to a spring. The collar 425 may be rotated about longitudinal axis 680 (i.e., longitudinal axis of the anvil 118). The collar 425 may define one or more notches 424 substantially complementary to one or more respective posts 423 fixed to, or integrally formed in, the anvil 118. In a locked arrangement, the collar 425 may be positioned in direction 432 distally away from the impactor 100 at a locked position, locking the attachment portion 422 within the connection mechanism 421, and the collar 425 is rotated about longitudinal axis 680 such that the one or more notches 424 do not align with the one or more posts 423. Impaction force and, in some embodiments, retraction forces are generated along longitudinal axis 680, causing accelerations and, thus, generating forces upon the collar 425 in the opposing direction 430 proximally toward the impactor 100. When the collar 425 is forced in direction 430, which is proximally toward the impactor 100, the lack of alignment of the one or more notches 424 and the one or more posts 423 may lock the collar 425 in the locked position to avoid travel of the collar 425 in direction 430 proximally toward the impactor 100. In an unlocked arrangement, the collar 425 is rotated about longitudinal axis 680 such that the one or more notches 424 align with the one or more posts 423. Once the one or more notches 424 are aligned with the one or more respective posts 423, the collar 425 has clearance to be forced in direction 430 proximally toward the impactor 100 to an unlocked position, thus releasing the attachment portion 422. It may be advantageous, especially with embodiments utilizing a double offset implement handle 106, to adjust the rotational position of the implement handle 106 with respect to longitudinal axis 680. Some embodiments may include a circular attachment portion 422 and circular defined aperture 426, such that any rotational position can be achieved. Some embodiments may include a circular attachment portion 422 with a key and a circular defined aperture 426 further defining one or more keyways, complementary to the key of the attachment portion 422. The number of rotational positions may be directly related to the number of keyways (e.g., one keyway may be one rotational position, two keyways may be two rotational positions, three keyways may be three rotational positions, etc.). Some embodiments may include the opposing arrangement (i.e., a key further defined by the defined aperture 426 and one or more keyways defined by the attachment portion 422). Some embodiments may include an attachment portion 422 and complementary defined aperture 426 that are symmetric shapes. For example, a rectangle may achieve two rotational positions, an equilateral triangle may achieve three rotational positions, a square may achieve four rotational positions, a pentagon may achieve 5 rotational positions, a hexagon may achieve 6 rotational positions, a heptagon may achieve 7 rotational positions, an octagon may achieve 8 rotational positions, etc. Some embodiments may include an attachment portion 422 that is splined and a defined aperture 426 includes a complementary spline socket profile. A spline and defined spline socket may include a plurality of rotational positions.

Figure 3A:
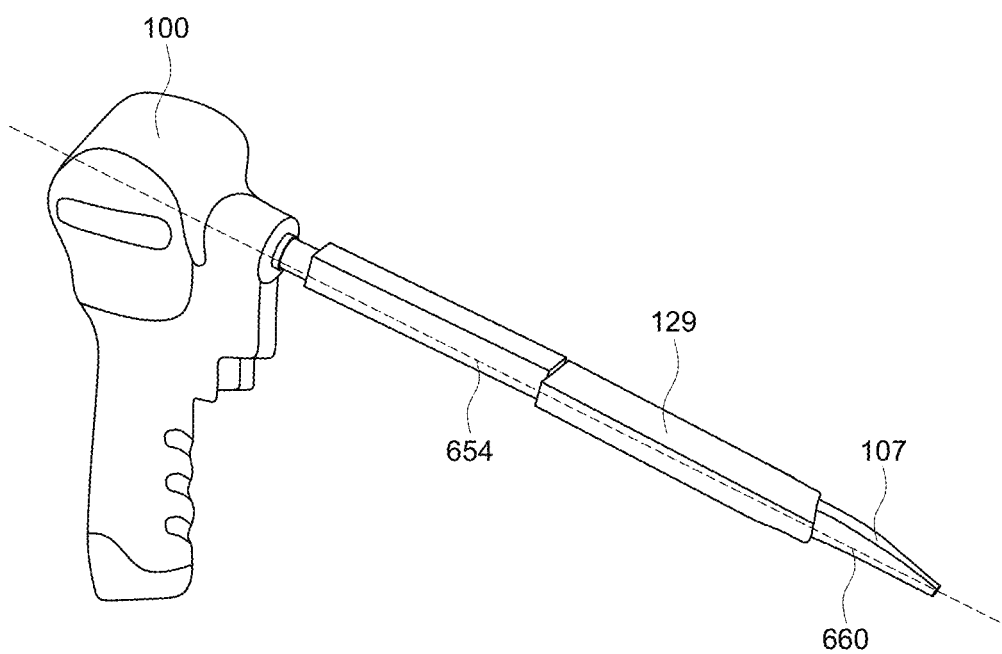
FIG. 3A illustrates an embodiment of an automatic impactor with a substantially linear implement handle.
Figure 3B:
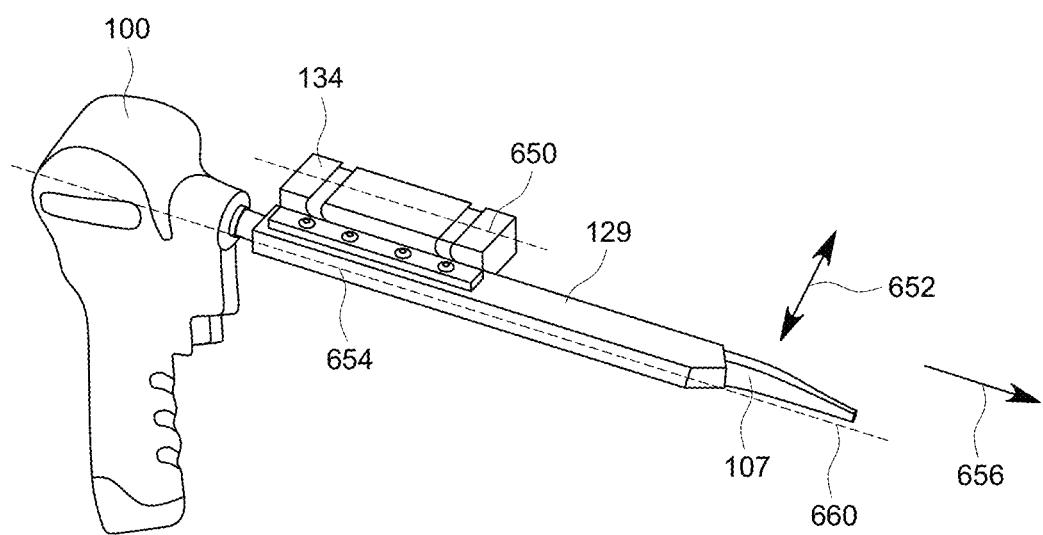
FIG. 3B illustrates an embodiment of an automatic impactor with a substantially linear implement handle and an eccentric rotating motor (ERM) for generating large amplitude vibrations.

In FIG. 3A, an illustration of a substantially linear implement handle 129 coupled to an impactor 100 is shown. The embodiment includes an implement handle 129 with a longitudinal axis 654 approximately parallel to a longitudinal axis 660 of the implement 107. The longitudinal axis 654 of the implement handle 129 and the longitudinal axis 660 of the implement 107 are approximately colinear. In some embodiments, the longitudinal axis 654 and the longitudinal axis 660 may also be approximately parallel and approximately colinear with the longitudinal axis 680 of the anvil 118, as shown in FIGS. 2B and 6A.

In FIG. 3B, an illustration of a substantially linear implement handle 129 is shown with a vibratory assembly 130 that generates high frequency vibrations. The illustrated embodiment includes vibration mechanism 134 (shown in FIG. 7) with a brush or brushless vibratory motor 135 (shown in FIG. 7), wireless communication electronics (e.g., a receiver, a transceiver, a microcontroller, etc.), vibratory motor battery, H-bridge or microcontroller, motor and electronics housing, and/or a manual switch or variable speed control 136. Alternatively, vibrations can also be generated with a piezoelectric or a mechanical device. The brush or brushless vibratory motor 135 and one or more eccentric weights 142 are shown in FIG. 7. The motor 135 drives the one or more eccentric weights 142 to rotate about the longitudinal axis 650 of the motor 135. As such, the vibration mechanism 134 may generate vibrations perpendicular to the longitudinal axis 650. When arranged as shown in FIG. 3B, the longitudinal axis 650 of the motor 135 is approximately parallel to the longitudinal axis 654 of the implement handle 129. As such, vibrations generated by the vibration mechanism 134 may be approximately perpendicular to the longitudinal axis 660 of the implement 107.

Figure 4A:
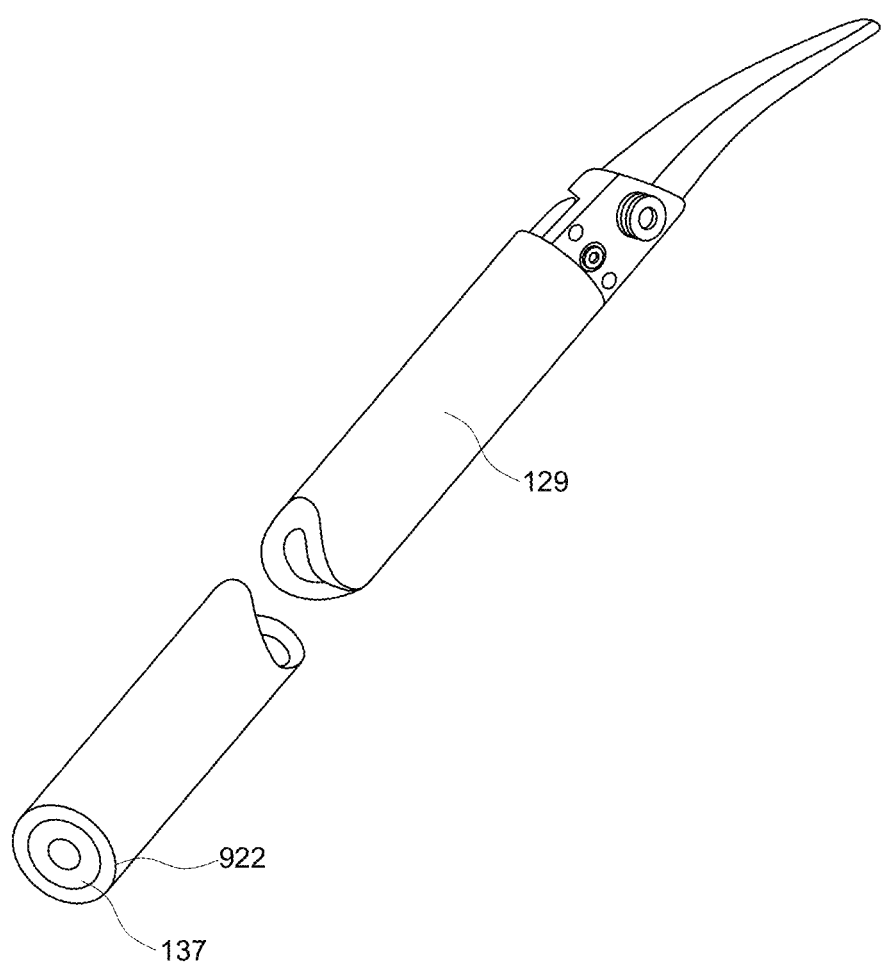
FIG. 4A illustrates an embodiment of a substantially linear implement handle.

In FIG. 4A, an illustration of a substantially linear implement handle 129 is shown with concentric elongate bodies or tubular bodies 922, 137. For example, elongate body 137 may be at least partially concentrically disposed in tubular body 922. Elongate body 137 may be used to prevent buckling of tubular body 922 during impact and to maintain stiffness. In some embodiments, tubular body 922 may be a stainless steel, aluminum, carbon steel, etc. tube. In some embodiments, elongate body 137 may be a carbon tube, stainless steel tube, fiberglass tube, Galvorn tube, a composite tube, or the like.

Figure 4B:
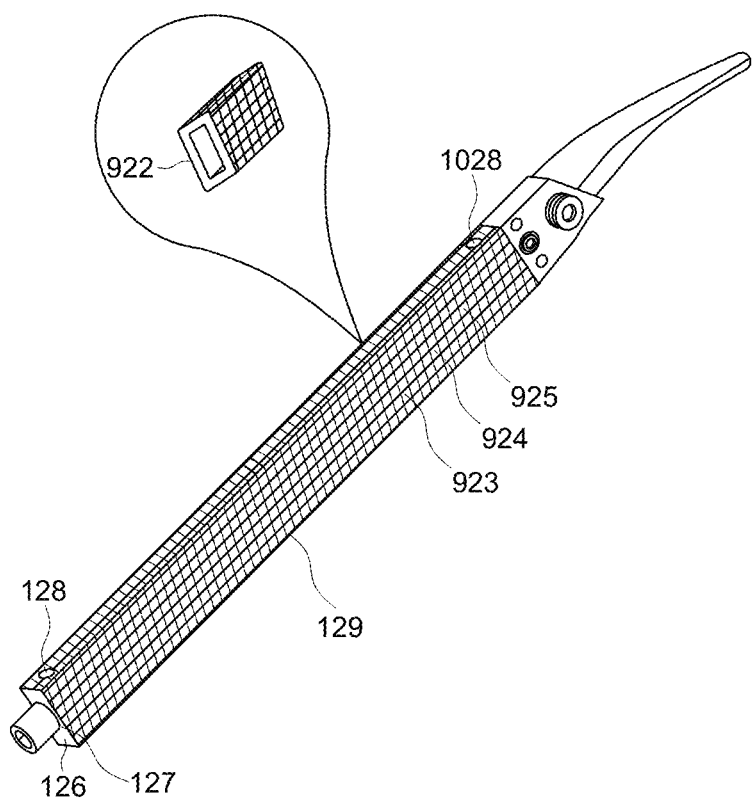
FIG. 4B illustrates an embodiment of an implement handle.

In FIG. 4B, a cross-sectional view of an embodiment of an implement handle 129 is shown. The implement handle 129 may be a polygonal shape, for example a tubular shape, a rectangular shape, or the like. Tubular body 922 may be covered by a weave 923 and infused with a resin 924. In some embodiments, the implement handle 129 may be baked to set the resin. Tubular body 922 may be made from or include stainless steel, aluminum, carbon steel, and the like. The weave 923 may be a woven carbon weave. The resin 924 may be an epoxy resin, a parylene resin, a polyurethane resin, a cyanoacrylate resin, a polyamide resin, a polyethylene resin, or the like. In some embodiments, a coating 925 is applied to create a hydrophobic surface to prevent humidity infusion in the resin 924 during sterilization cycles (e.g., using an autoclave or other high pressure and/or high temperature protocol). The coating 925 may also prevent humidity related discoloration issues (e.g., a milky appearance). The weave 923 can be woven with a herringbone weave and the pick count (number of carbon fibers per inch or metric measurement) may increase at the outside bend radius 926 of the tubular body 922. Other weave patterns can include twill, satin, etc. for improved formability and strength. The tubular body 922 may have a thickness of about 0.25 mm to about 2 mm; about 0.3 mm to about 1.75 mm; about 0.4 mm to about 1.5 mm, etc. The use of tubular body 922, along with a weave system, can reduce the weight of a standard broach handle 129 by as much as about 50% over a standard stainless steel implement handle. For example, a standard stainless steel implement handle can weigh as much as about 0.91 kg (2 lbs. of force). Additionally, the combination of materials in the embodiment described herein achieves increased weight to stiffness ratios. The improved weight to stiffness ratios allows for effective force and vibration transmission. Stiffness is a function described as force divided by the amount of bending. Furthermore, the weave 923 and resin 924 may also prevent the tubular body 922 from buckling during impact. A distal plug 126, along with an attached spud, may be coupled to the distal end of the tubular body 922 by spinning, ultrasonic welding, tungsten inert gas (TIG) or laser welding, or fitted to the distal end of the tubular body 922. A collar 127 with locking mechanism may be attached over the spud of the distal plug 126. A defined potting hole 128, that may be plugged by a plug, may serve as a receptacle for resin 924 dispersion inside the collar 127. Resin 924 dispersion may be accomplished by flowing resin in through the potting hole 128 to fill the defined volume of the tubular body 922. Air escaping may exit through a defined exhaust hole 1028 until resin reaches the defined exhaust hole 1028. An inverse of this described process is also possible in which the resin enters the exhaust hole 1028 and air escapes from the potting hole 128. The weave 923 may be fitted over the bent tubular body 922 and inside the collar 127. The tubular body 922 can be bent into a number of configurations including, but not limited to, single offset and double offset as an example. The plug with an attached spud is also fitted to the proximal end of the implement handle 106 as described herein. A collar 127 is also attached to the plug. The collars 127 may have an undercut on the inside surface. Resin 924 is then dispersed through the potting hole(s) 128 and then baked in a high pressure and/or high temperature device (e.g., autoclave). Once set, the resin 924 may serve to lock the weave 923 in place. The weave locks in place because of the undercut on the inside surface of the collars 127. The weave 923 with resin 924 can have up to five times the strength of stainless steel. The proximal plug is configured to fit to the connection mechanism 105. As an alternative to the embodiment described herein, elongate body (ies) 137 can be inserted into substantially linear (nonplanar) tubular body 922 sections, and interfaces 138 (e.g., machined stainless steel, diecast stainless steel, etc.) can serve as the bent offsets. The interfaces 138 with integral spuds can be press fitted, bonded, laser, spun, TIG, or ultrasonically welded into the nonplanar sections of the tubular body 922. The design of the described assembly is such that the outside joint surfaces may be flush with one another.

Figure 5:
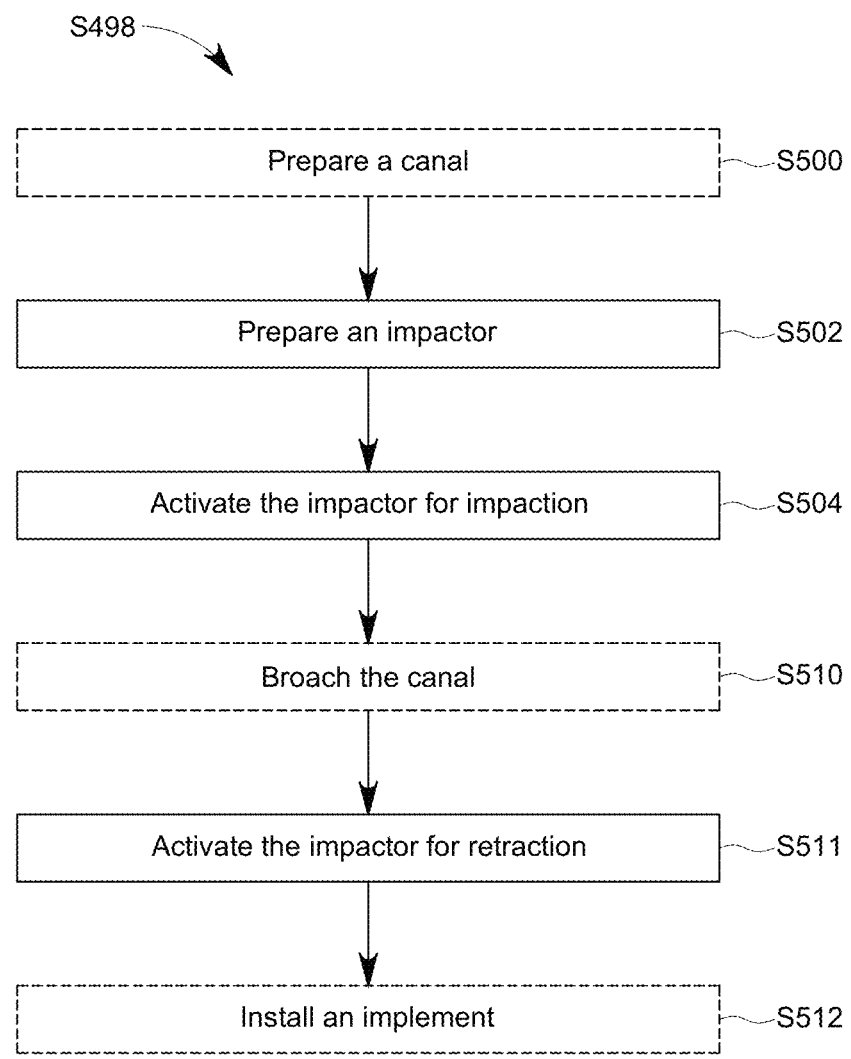
FIG. 5 is a block diagram of a method of using an embodiment of an automatic impactor system.

FIG. 5 shows a block diagram of a method S498 for using an impactor 100. The method includes optionally preparing a bone for broaching in block S500; preparing an impactor in block S502; activating the impactor in block S504; optionally broaching the canal in block S510; and optionally installing an implement in block S512. In some embodiments, the method functions to install an implement in the canal of the bone. In some embodiments, the method, for example, in the absence of blocks S500, S510, and/or S512 may be used for impaction of a tool (e.g., a chisel, a file, a tamp, or the like) and/or installment of an implement (e.g., a nail or the like). The method S498 can be configured and/or adapted to function for any suitable operation.

As shown in FIG. 5, an embodiment of a method S498 for using an impactor 100 includes optional block S500, which recites preparing a bone for broaching. For example, the surgeon may prepare a bone for broaching in the femur during hip surgery by removing the acctabulum. In some embodiments, the humeral canal during shoulder surgery may be prepared for broaching by removing the humeral head. Preparing a bone for broaching may further include preparing the cut bone surface, and reaming or drilling the femur medullary canal or, in shoulder surgery, the humeral canal.

As shown in FIG. 5, an embodiment of a method S498 for using an impactor 100 includes block S502, which recites preparing an impactor. The impactor 100 is prepared for surgery by attaching an appropriate implement handle 106 or implement handle 129 (shown in FIGS. 1A and 3A) and attaching a succession of small to large implements (e.g., broaches or stems shown in FIG. 2A). Additionally, the implement handle 106 may be rotationally positioned to an advantageous position about longitudinal axis 680 (as described for FIG. 2B). An advantageous position may increase access to a working site, leverage for the user, and/or ergonomics.

Figure 10A:
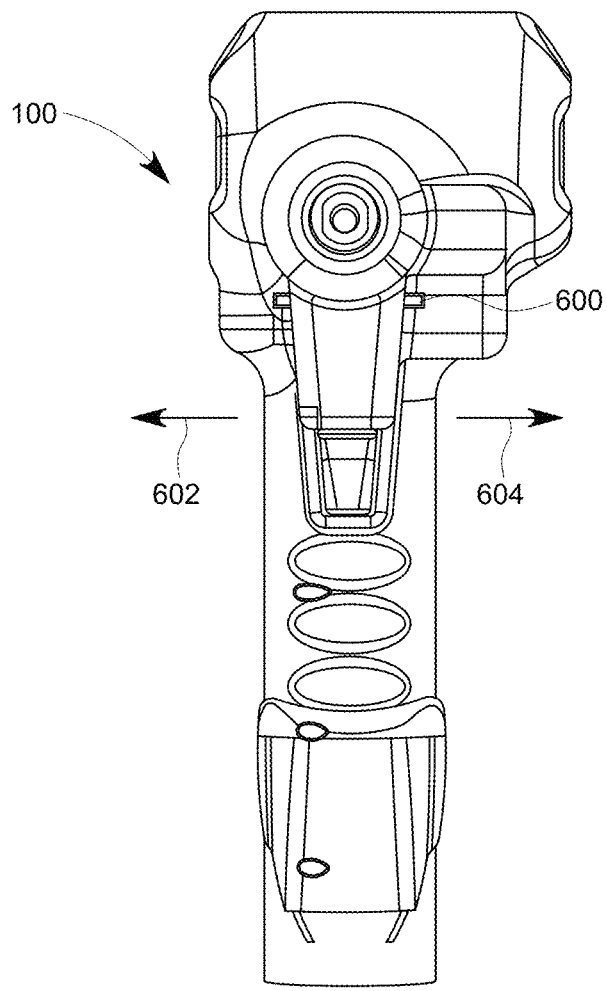
FIG. 10A illustrates an embodiment of mode selector input of an impactor.
Figure 10B:
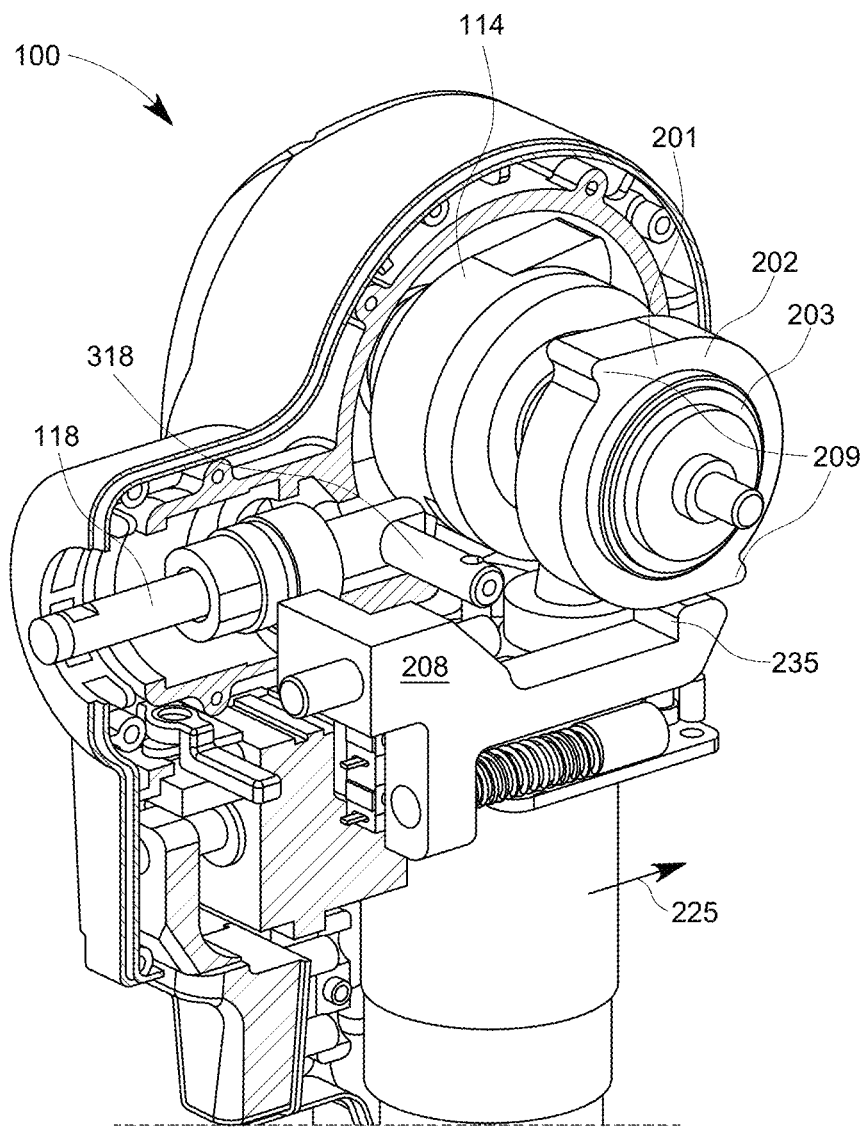
FIG. 10B illustrates the internal mechanisms an embodiment of an impactor mechanism, including a retractor mechanism.
Figure 10C:
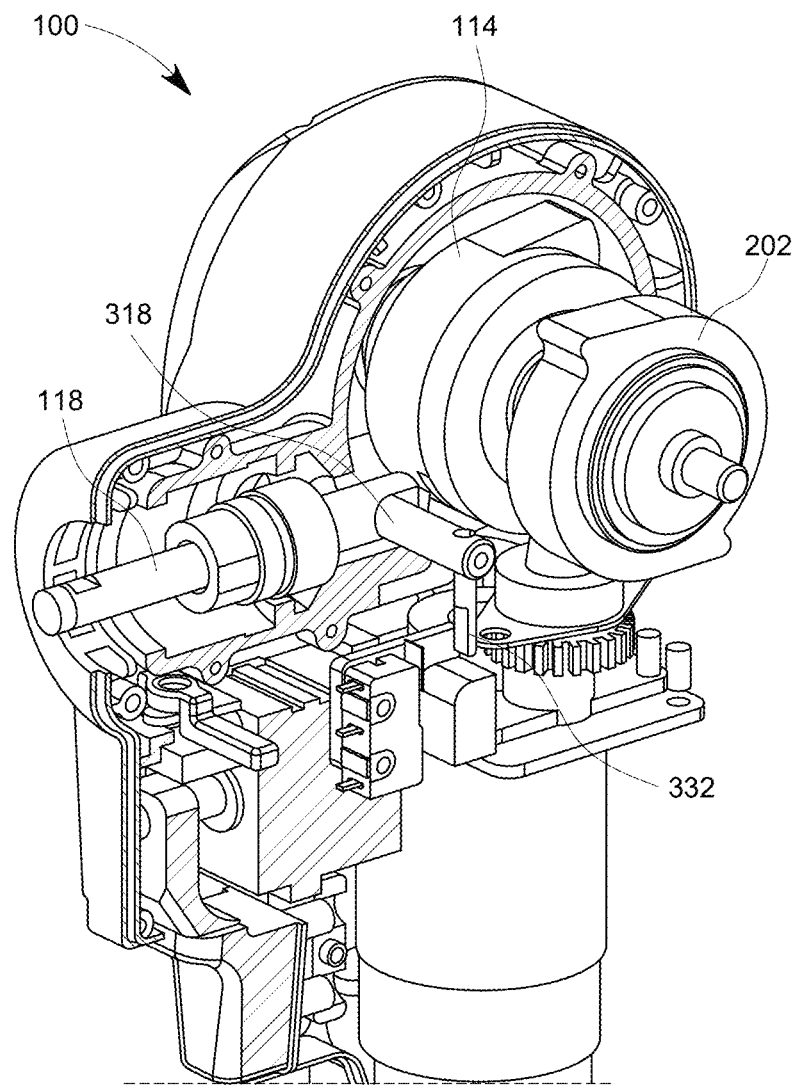
FIG. 10C illustrates the internal mechanisms an embodiment of an impactor mechanism with the retractor removed.

As shown in FIG. 5, an embodiment of a method S498 for using an impactor 100 includes block S504, which recites activating the impactor. The impactor 100 may operate with, for example, a 12, 18, 20, or 24-volt DC variable speed battery powered electrical system. The battery 101 provides current or motive power through a controller 110 such as an H-Bridge or equivalent. The controller 110 changes the frequency and thus the speed of the motor 108 when the control input 103 is depressed. One or more polyfuses 111 serves to protect the electrical components from a large current in rush or back electromotive force when the control input 103 is fully depressed or released quickly. In some embodiments, the motor 108 is brushless and autoclavable. Alternatively, a brush motor may be employed. The cam system serves to turn rotary motion into linear motion so that an anvil 118 that is connected to the implement handle 106 (or implement handle 129 shown in FIG. 4B) imparts the impact force to the attached implement 107. Activating the impactor 100 may include driving a driveshaft 121 in a first rotation direction 682 (shown in FIG. 6A) (i.e., counterclockwise) to drive an impaction cam 114 operatively coupled to the driveshaft 121. Activating the impactor 100 may include impacting an anvil 118 with the impaction cam 114 such that the anvil 118 is driven in an impaction direction 125 distally away from impaction cam 114. Activating the impactor 100 may include, when a minimum force is sustained by the anvil 118, disengaging the impaction cam 114 from the anvil 118 by allowing retardation of the impaction cam 114 with respect to the driveshaft 121 and translating the impaction cam 114 in a second axial direction 685 (shown in FIG. 10E) toward spring 113 along a longitudinal axis 681 of the driveshaft 121 until the lobe is out of contact with the anvil 118. Activating the impactor 100 may include forcing the impaction cam 114 back in a first axial direction 684 away from spring 113 to an impaction position for a subsequent impact.

As shown in FIG. 5, an embodiment of a method S498 for using an impactor 100 includes optional block S510, which recites broaching the canal. For example, the surgeon may broach the femur medullary canal and an implement 107 (e.g., a final broach) may be used to prepare the medullary canal for a final fitting and/or impaction of the implement 107. For example, the surgeon may broach the humeral canal and an implement 107 (e.g., a final broach) may be used to prepare the humeral canal for a final fitting and/or impaction of the implement 107.

As shown in FIG. 5, an embodiment of a method for using an impactor 100 includes block S511, which recites activating the impactor for retraction. Activating the impactor for retraction may include driving a driveshaft 121 in a second direction 683 (shown in FIG. 6A) (i.e., clockwise) to drive a retraction cam 202 (shown in FIG. 10B). Activating the impactor 100 for retraction may include impacting a retractor 208 (shown in FIG. 10B) using the retraction cam 202 such that the retractor 208 drives the anvil 118 in a retraction direction 225 proximally toward impaction cam 114.

As shown in FIG. 5, an embodiment of a method S498 for using an impactor 100 includes optional block S512, which recites installing a stem. The surgeon performs a final fitting and/or impaction of the implement 107.

FIG. 6A shows an embodiment of an impaction cam system. The impaction cam 114 may include an eccentric profile with cam lobes 140. In some embodiments, the motor 108 (shown in FIG. 1B) drives the gear train to rotate a driveshaft 121 and, in turn, the impaction cam 114 rotates eccentrically. The anvil 118 may be in sliding contact with the cam lobe 140. When a cam lobe 140 strikes the anvil 118, a force is imparted on the anvil 118 in direction 125 along a longitudinal axis 680 of the anvil 118. Direction 125 is directed distally away from the impaction cam 114 along the longitudinal axis 680 toward the implement handle 106 (shown in FIG. 1A)

FIG. 6B shows another view of the impaction cam system, including the impaction cam 114, the gear train, and the conical spring 113. The gear train of some embodiments include a ring gear 117a driven by a conical pinion 117b. As the ring gear 117a is driven to rotate, the ring rear gear 117a, operatively coupled to the driveshaft 121, drives the driveshaft to rotate. The arrangement of the conical pinion 117b operatively coupled to the ring gear 117a may be illustrated in FIG. 10D.

Figure 6C:
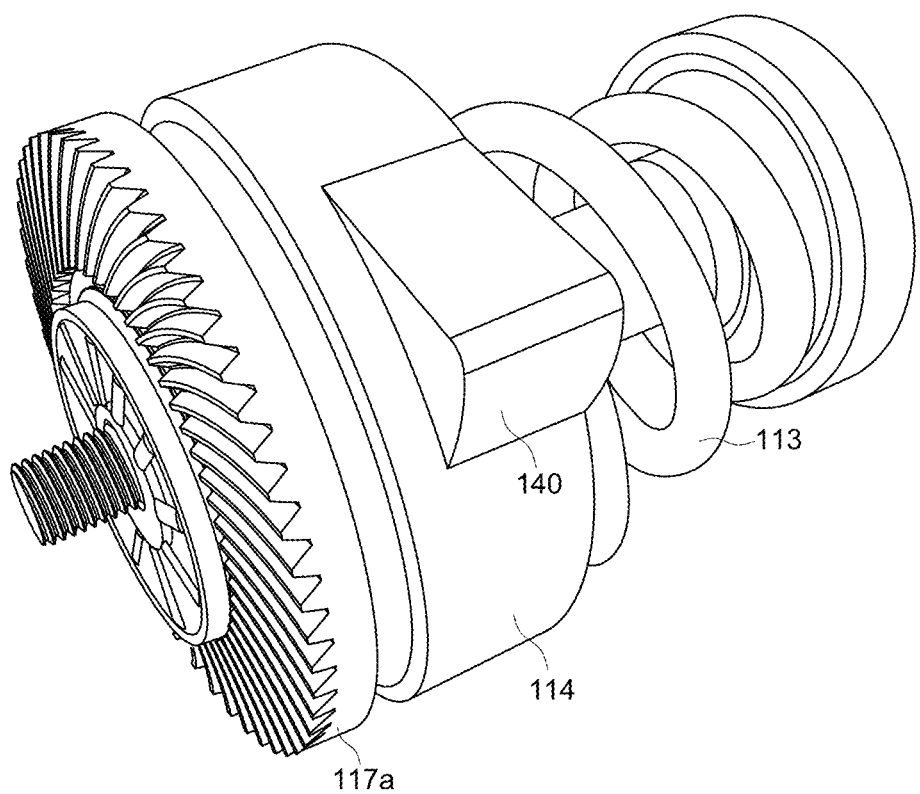
FIG. 6C illustrates a perspective view of a cam assembly including a conical spring.

FIG. 6C shows an embodiment of an impaction cam system. The impaction cam 114 includes two opposing cam lobes 140, shown in FIG. 6A. The impaction cam 114 may be driven to rotate in a direction, for example rotation direction 682 (i.e., counterclockwise), by a motor 108 (shown in FIG. 1B) and gear train, for example a conical pinion 117b and ring gear 117a (FIG. 6B). The cam system includes the impaction cam 114 forced upon by a conical spring 113, which may be preloaded.

Figure 6D:
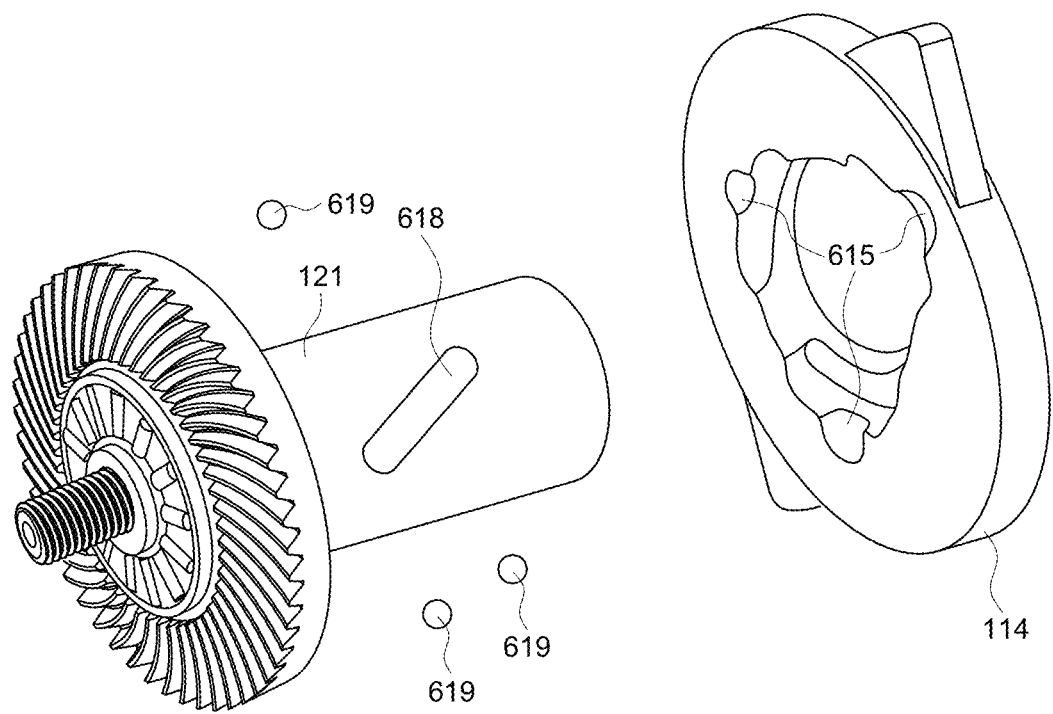
FIG. 6D illustrates an exploded view of the cam assembly of an impaction device.

FIG. 6D illustrates the operative coupling of the impaction cam 114 to the driveshaft 121. The driveshaft 121 may define a plurality of spherical grooves 618 that are complementary to a plurality of respective ball bearings 619. The spherical grooves 618 are complementary due to the radius of the grooves 618 being approximately equal to the radius of the ball bearings 619. The impaction cam 114 defines a plurality of sockets 615 that are complementary to the respective ball bearings 619. The impaction cam 114 operatively couples to the driveshaft 121 with the plurality of ball bearings 619 restrained in the respective grooves 618 and respective sockets 615. Each spherical groove 618 includes approximately matching profiles and angular spacing from one another. As such, the impaction cam 114 may rotate with respect to the driveshaft 121 along the profiles of the spherical grooves 618. When the impaction cam 114 is driven to rotate with respect to the driveshaft 121 in a first rotation direction 682 (shown in FIG. 6A) (i.e., counterclockwise), the impaction cam 114 may be advanced in a first axial direction 684 (shown in FIG. 10E) away from the spring 113. The profile of the plurality of grooves 618 advances the impaction cam 114 in direction 684 away from the spring 113, and may cease at, a position appropriate for striking the anvil 118 (shown in FIGS. 6A, and 10A-10F). When the impaction cam 114 is driven to rotate with respect to the driveshaft 121 in a second rotation direction 683 (i.e., clockwise) (shown in FIG. 6A), the impaction cam 114 may be retracted in a second axial direction 685 (shown in FIG. 10E) toward the spring 113. The profile of the plurality of grooves 618 retracts the impaction cam 114 in direction 685, compressing spring 113 (shown in FIGS. 6C and 10E) and retracting impaction cam 114 out of contact with the anvil 118 (shown in FIGS. 6A, and 10A-10F).

The impaction process has the advantage of rapidly striking the anvil 118 with the impaction cam 114 and disengaging contact between the impaction cam 114 and the anvil 118. When the motor 108 (shown in FIG. 1B) drives the driveshaft 121 to rotate in rotation direction 682 (shown in FIG. 6A) (i.e., counterclockwise), the impaction cam 114 rotates with driveshaft 121, establishing angular kinetic energy. As a cam lobe 140 of the impaction cam 114 strikes the anvil 118, the angular kinetic energy is transferred from the impaction cam 114 to the anvil in direction 125 along the longitudinal axis 680 of the anvil 118. When the anvil 118 withstands the force generated by the impaction cam 114 impact, the impaction cam 114 may be driven backwards with respect to the driveshaft 121. Said another way, the rotation of the impaction cam 114 may be retarded by the impact and rotate in rotation direction 683 (i.e., clockwise) with respect to the driveshaft 121 when the force transferred into the anvil is sustained by the anvil (i.e., the anvil 118 sustains a minimum force). A minimum force to cause rotation of the impaction cam 114 in rotation direction 683 (i.e., clockwise) with respect to the driveshaft 121 may be equal to or greater than impaction forces described herein (i.e., about 330 N (75 lbs. of force) to about 890 N (200 lbs. of force); about 440 N (100 lbs. of force) to about 800 N (180 lbs. of force); about 550 N (125 lbs. of force) to about 775 N (175 lbs. of force); etc.). Rotation of the impaction cam 114 in rotation direction 683 (i.e., clockwise) with respect to the driveshaft 121 causes the impaction cam 114 to translate axially in direction 685 toward spring 113, compressing spring 113 (e.g., a conical spring) until contact between the cam lobe 140 of the impaction cam 114 and the anvil 118 is ceased. After the cam lobe 140 of the impaction cam 114 slides past the anvil 118, the spring 113 decompresses and advances the impaction cam 114 back in direction 684. While advancing the impaction cam 114 in direction 684, the impaction cam 114 is driven to rotate at a more rapid rate than the driveshaft 121, thus causing the impaction cam 114 to rotate in rotation direction 682 with respect to the driveshaft 121. The impaction cam 114 angularly accelerates as it advances in direction 684 until it moves into the appropriate position to once again strike the anvil 118 and repeat the process. The impaction process may be advantageous in that: the motor 108 (shown in FIG. 1B) does not stall when the anvil 118 sustains the impaction force of the impaction cam 114, the rotation rate of the driveshaft 121 is substantially constant, and the process produces high-frequency, low force impacts.

Figure 8:
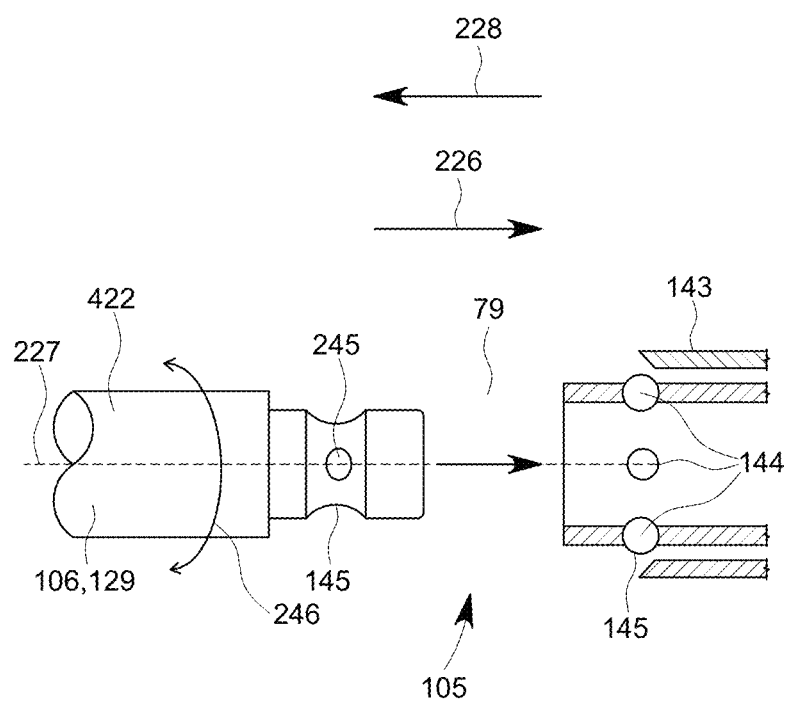
FIG. 8 illustrates an embodiment of an implement connection mechanism that provides various degrees of orientation of the implement handle relative to the automatic impactor.

FIG. 8 illustrates an embodiment of a connection mechanism 105. Although there are many approaches to a connection mechanism as defined herein, the illustrated example employs a ball detent 79 system. To decouple the implement handle 106 (or implement handle 129 shown in FIG. 4B) from the connection mechanism 105, the collar 143 is slid in direction 226 (in some embodiments against a bias force such as a spring), disengaging the collar 143 from one or more balls 144. Disengaging the collar 143 from the one or more balls 144 allows the one or more balls 144 to move away from the longitudinal axis 227 and out of engagement with a detent 145 defined by the attachment portion 422. At this point, the attachment portion 422 is free to be removed from the connection mechanism 105. Coupling the attachment portion 422 into the connection mechanism 105 may be done by sliding the collar 143 in direction 226 away from the implement handle 106, allowing the aforementioned clearance of the one or more balls 144 with respect to the attachment portion 422 as it is slid into place. The collar 143 may then be returned in direction 228 toward the implement handle 106 such that the collar 143 removes the clearance that allow the one or more balls 144 to move away from the longitudinal axis 227, thus locking the one or more balls 144 in the detent 145. Some embodiments include a connection mechanism 105 with rotational locking capabilities. For example, the detent 145 may further include one or more defined sockets 245 complementary to the one or more balls 144. As such, once the one or more balls 144 are engaged in the detent 145, the attachment portion 422, and thus the implement handle 106 (or implement handle 129 shown in FIG. 4B), may be rotated 246 about the longitudinal axis 227 until the one or more balls 144 engage with the one or more respective sockets 245. The collar 143 may be allowed to advance further in direction 228 toward the implement handle 106 further reducing the clearance allowing the balls 144 to move away from the longitudinal axis 227. As such, embodiments with two or more balls 144 and two or more respective sockets 245 may achieve two or more respective rotational positions that are lockable about the longitudinal axis 227.

Figure 9:
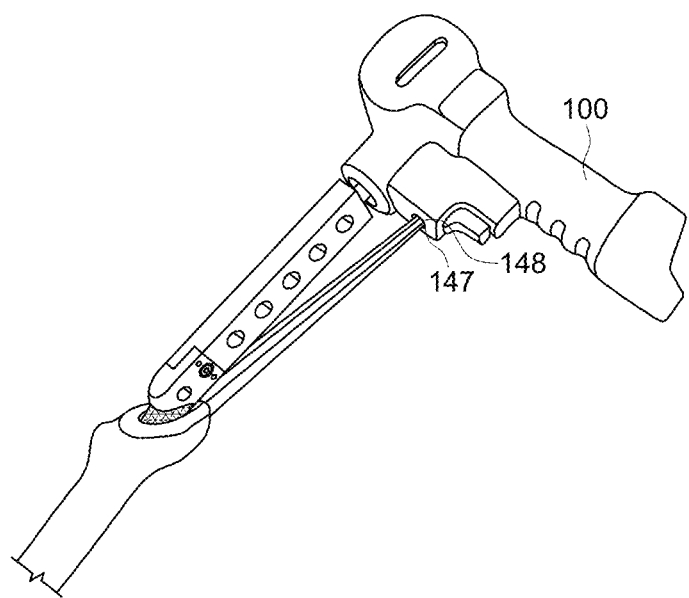
FIG. 9 illustrates an embodiment of a camera with a light source trained on a bone.

FIG. 9 shows a camera 147 aligned to record the working space and one or more lights 148 aligned to illuminate the working space. In some embodiments, the camera 147 is of sufficient resolution, for example about 50 PPI (pixels per inch) to about 200 PPI, about 60 PPI to about 180 PPI, about 70 PPI to about 150 PPI, etc. A camera module such as Arduino or equivalent with a 4-to-8-megapixel resolution and sufficient focal length to establish picture clarity may be used. A 1× to 2× magnification may be sufficient to see potential hairline cracks. In some embodiments, higher magnification may reduce the field of view. An about 90 degrees to about 120 degree field of view or a fisheye lens may be sufficient for many cortical rim hairline cracks in femurs, for example. Once the broaching is complete and the stem is installed, the view can be memorialized by employing a wireless transmitter connected to the camera to capture the image on a computing device (e.g., cell phone, computer, tablet, etc.). Further, in some embodiments, a microcontroller or other processor may convert the image to gray scale. Gray scale may provide sharper contrast and help to visualize hairline cracks. A swab containing dilute methylene blue powder or methylene blue liquid may be applied. In some embodiments, the swab is diluted greater than about 50% with about 70% or more alcohol concentration. The alcohol in the methylene blue solution reduces the surface contact angle and wets the surface more easily. The methylene blue solution, as a result, more easily seeks a hairline crack making it visible even with an unaided eye. The methylene blue solution can be wiped away with a second clean or alcohol infused swab. The alcohol concentrations can be varied but can be above about 70%. The dilutions with alcohol can be varied but concentrations above about 50% may be sufficient.

Surgical light may be sufficient. However, the surgical area is often a blind hole. A light emitting diode (LED) having a wavelength of about 365 nm to about 450 nm, or about 450 nm to about 490 nm may be used to improve contrast.

FIGS. 13A-14B shows an embodiment of a reversing mechanism that facilitates the removal or extraction of broaches, stems, nails or any medical or commercial implement. The vibratory assembly 130, along with an eccentric weight 142, can facilitate or completely remove or extract an implement (e.g., broach, stem, nail, medical equipment, commercial equipment, etc.). However, in some embodiments, additional, or reverse, impact force may be used to remove or extract the items listed. A double opposing eccentric cam (i.e., impaction cam 114) may also be used. Either cam is engaged by shifting a shaft 167 in and out. In this way, the motor 108 can be run in reverse or forward.

Figure 12:
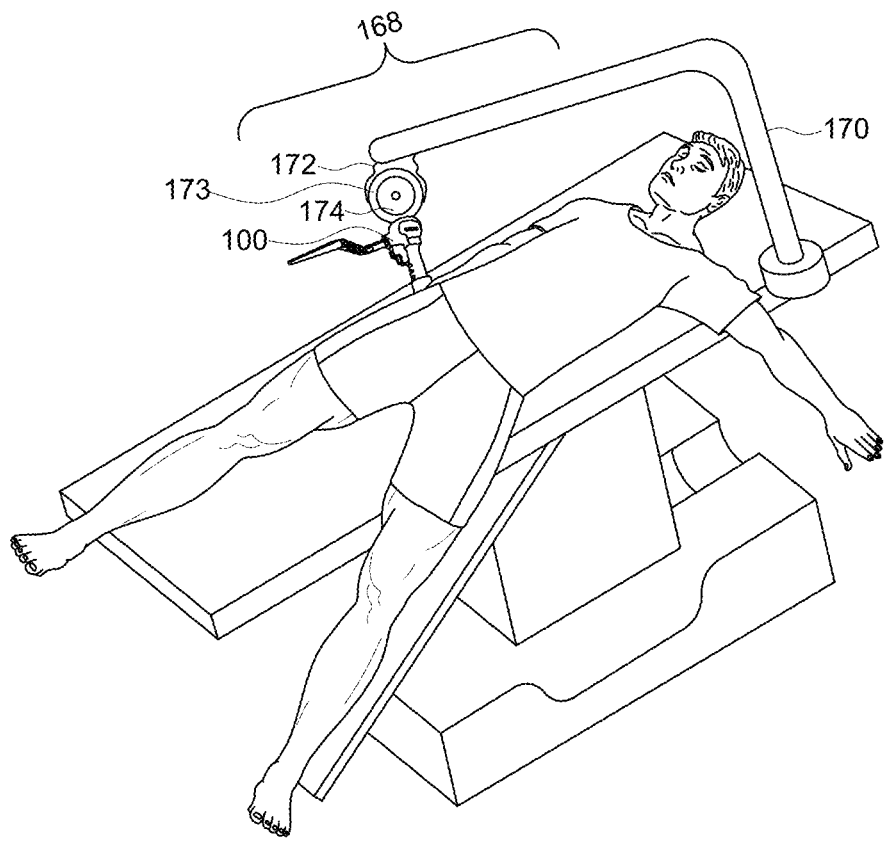
FIG. 12 illustrates an embodiment of a balancer connected to an impactor with a sheath.
Figure 13A:
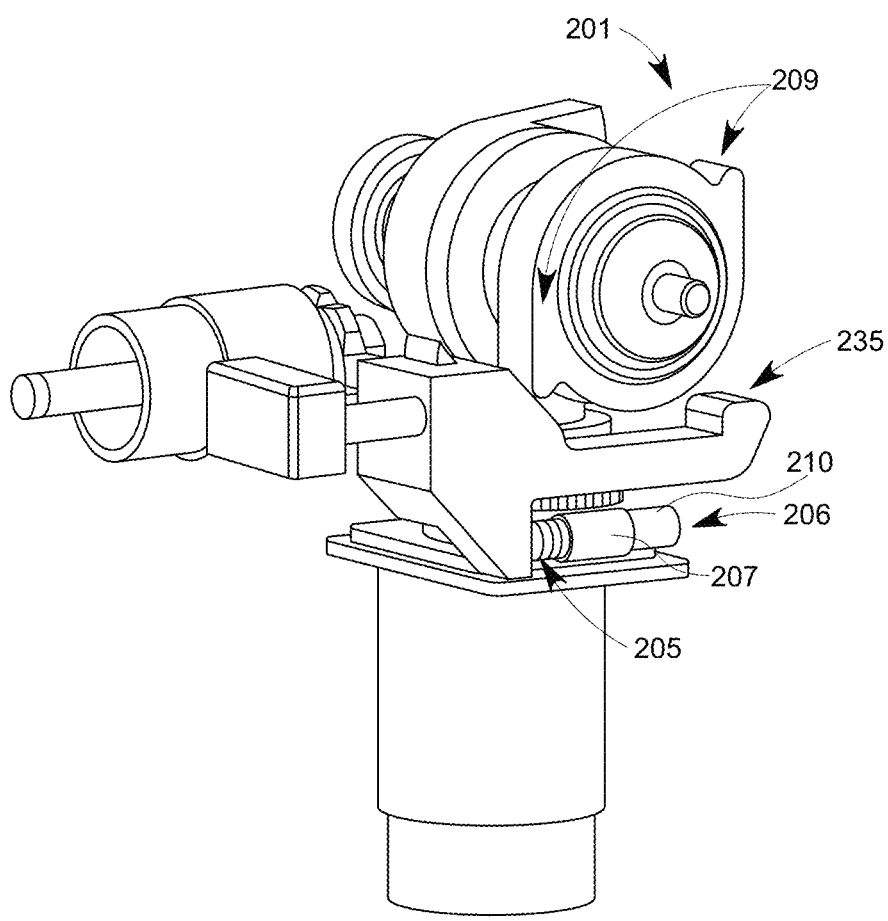
FIG. 13A illustrates an embodiment of a retraction assembly of an impaction device.
Figure 13B:
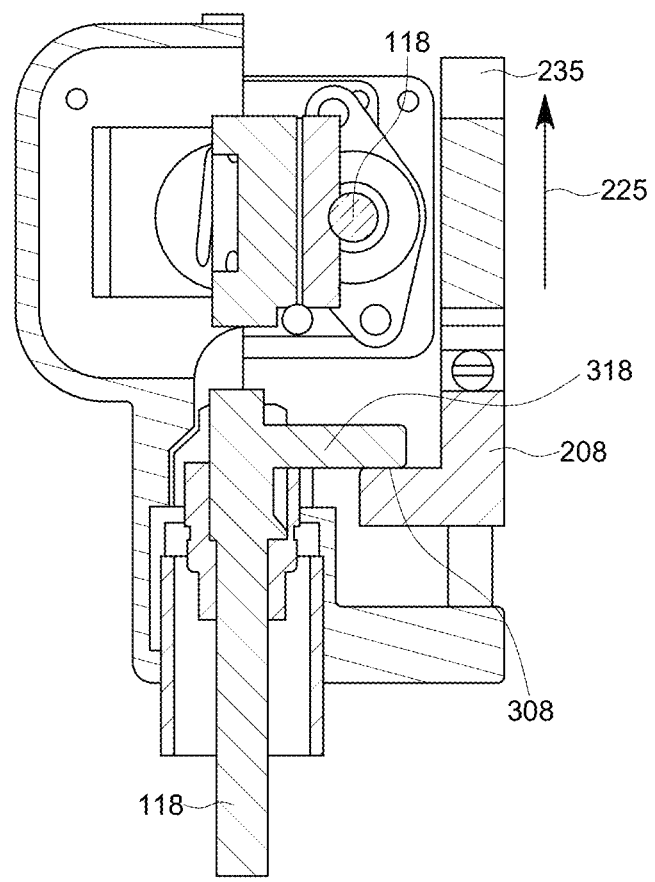
FIG. 13B illustrates a perspective view of the retraction assembly of FIG. 13A.

FIG. 12 illustrates a tool balancing system 168. Embodiments of the impactor 100 may weigh approximately 4.5 lbs. (2.04 kg) to 5.5 lbs. (2.49 kg). Even though embodiments described include a lighter weight than other known commercial impactors, use over time, for example, a 30-minute period, may tire a surgeon. The effect of impactor 100 weight can be reduced by employing a tool balancer 169 that may be hung on the surgery room ceiling or on an arm 170 connected to a patient support apparatus (e.g., bed, gurney, etc.). A sterile disposable sheath 172 can include a flexible wire with a hook 173 that connects to the fulcrum of the impactor 100. A force adjustment knob 174 can be accessed through the sheath 172.

FIGS. 10B, 10F, 13A and 13B show an impactor 100 that includes a retraction mechanism 201. It may be advantageous that the impactor 100 include mechanical retraction capability. The retraction mechanism 201 employs a retraction cam 202 that is engaged when the motor 108 is reversed to rotate the driveshaft 121 in rotation direction 683 (shown in FIG. 6A) (i.e., clockwise). The retraction cam 202 is operatively coupled to the driveshaft 121 using a one-way bearing 203. As such, the one-way bearing 203 does not engage when the driveshaft 121 is driven to rotate in rotation direction 682 (shown in FIG. 6A) (i.e., counterclockwise). The one-way bearing 203 may engage to drive the retraction cam 202 when the driveshaft 121 is driven to rotate in rotation direction 683. When the retraction cam 202 rotates in rotation direction 683, the lobes 209 may contact a cleat 235 of a retractor 208 and drive cleat 235 in a direction 225, parallel and opposite of the drive direction 125 (shown in FIG. 6A) of the anvil 118. The anvil 118 includes a retraction bar 318 (shown in FIGS. 10B-10F) which is in interference with a strike portion 308 of the retractor 208. As such, when the retractor 208 is driven back in direction 225, the strike portion 308 may contact the retractor 208 to drive the anvil 118 back in direction 225.

Figure 10D:
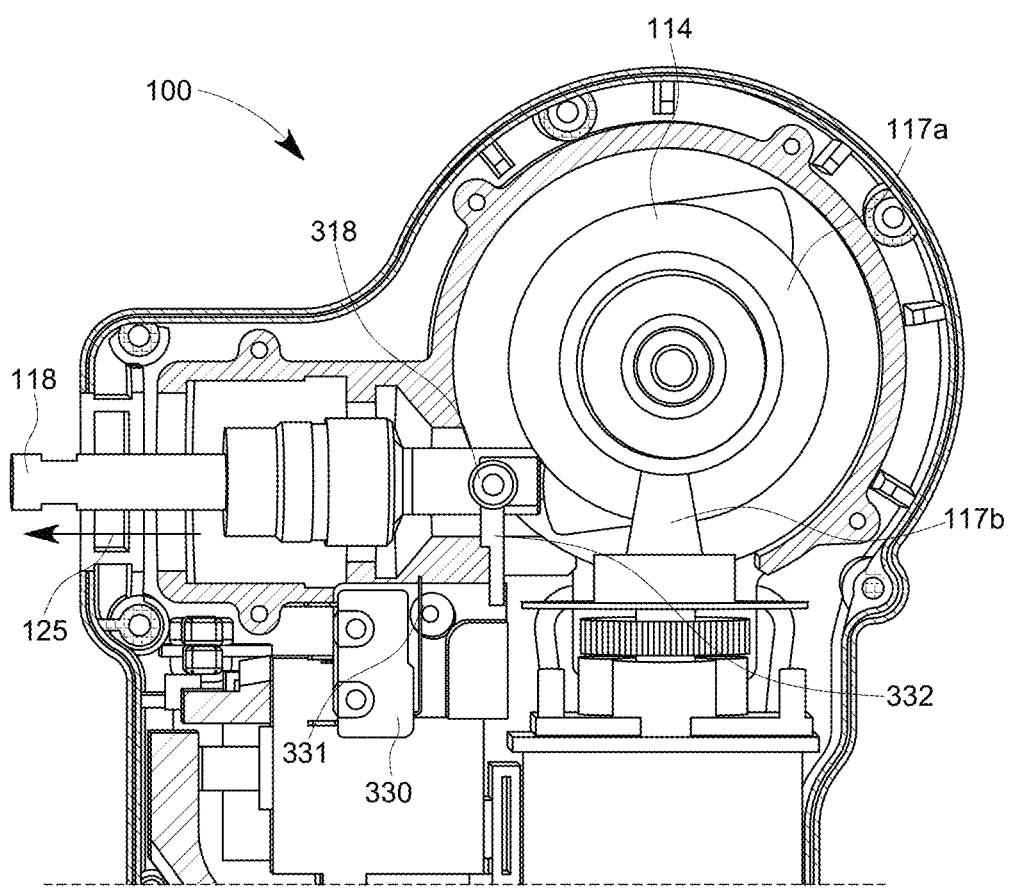
FIG. 10D illustrates the internal mechanisms an embodiment of an impactor mechanism with the retractor and retraction cam removed.
Figure 10E:
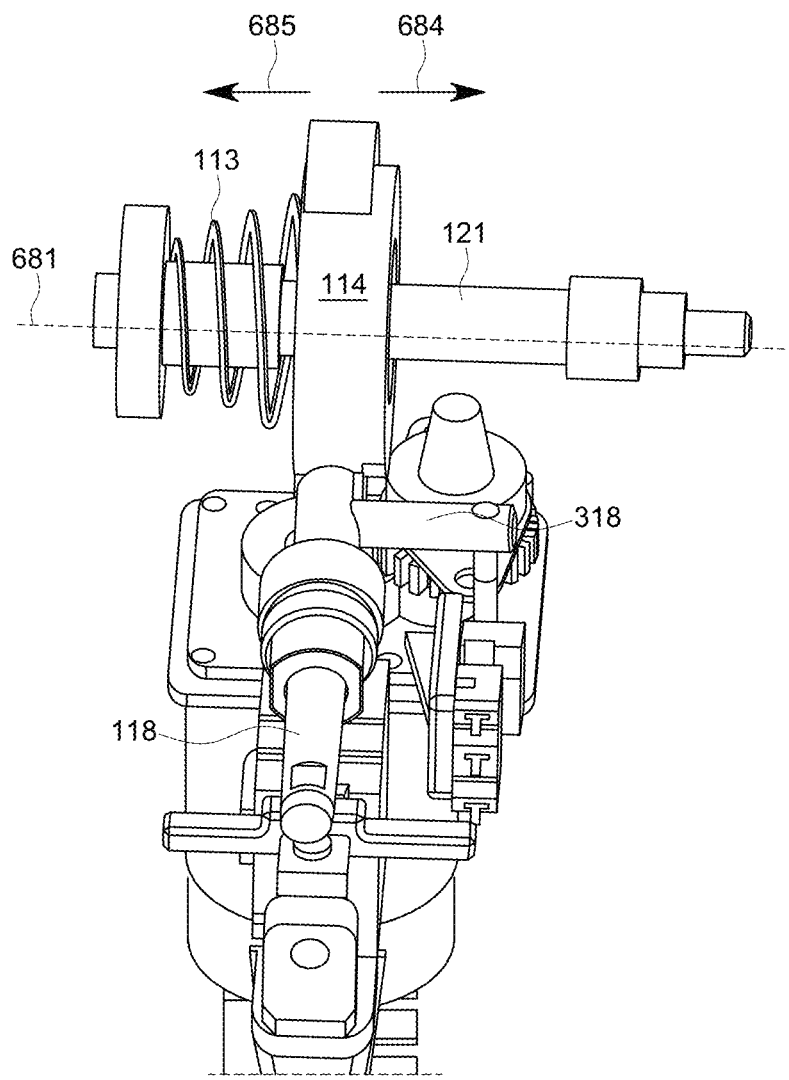
FIG. 10E illustrates a perspective view of an embodiment of an impaction mechanism of an impactor.
Figure 10F:
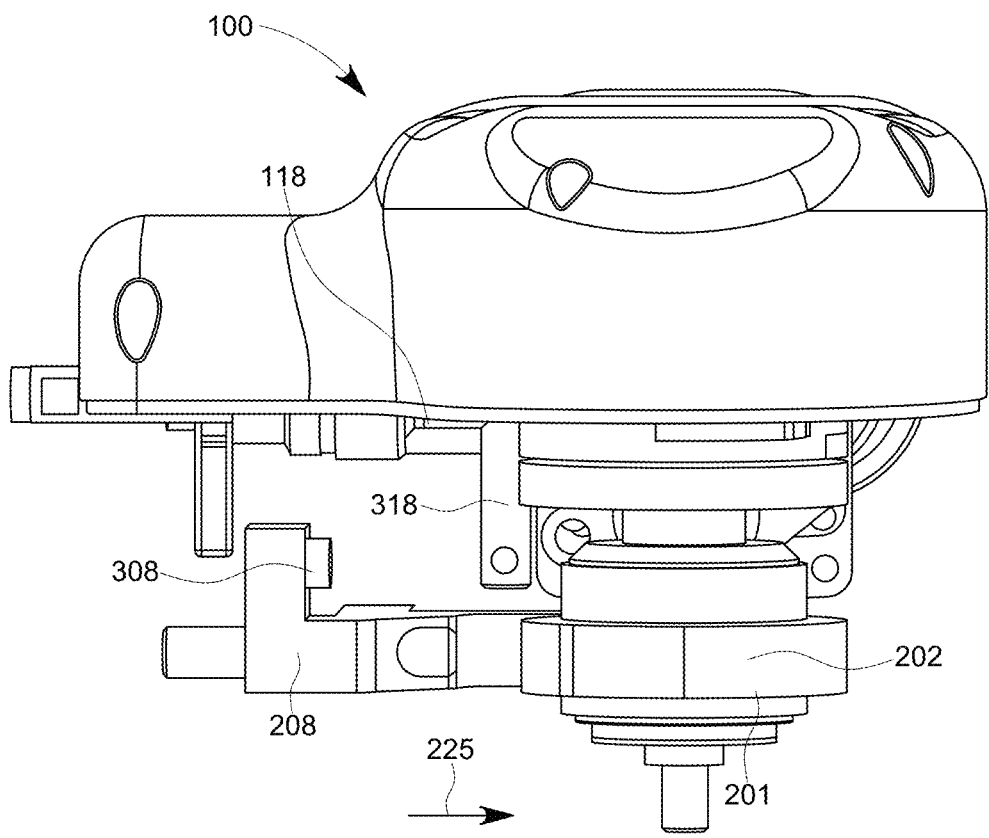
FIG. 10F illustrates a top-view perspective of a retraction mechanism of an embodiment of an impactor.

As illustrated in FIG. 10D, some embodiments may include a retraction switch 330 for indicating one or more conditions for retraction. For example, some embodiments may retract when the anvil 118 is pulled in direction 125 distally away from the impaction cam 114 and out of contact with impaction cam 114. To indicate that the anvil 118 is pulled far enough in direction 125 that the impaction cam 114 will not contact the anvil 118, the retraction bar 318 may include a limit bar 332. When the anvil 118 is pulled far enough in direction 125, the limit bar 332 may contact a limit lever 331 of the retraction switch 330, actuating the retraction switch 330. Some embodiments may not power the motor 108 (shown in FIG. 1B) in a direction to drive the driveshaft 121 in rotation direction 683 (i.e., counterclockwise) unless the retraction switch 330 is properly actuated. The impactor 100 may facilitate the removal or extraction of implements (e.g., broaches, stems, nails or any medical or commercial implement). For example, the impactor 100 may be pulled back such that the anvil 118 is slid to a forward position along direction 125 distally away from the impaction cam 114. Once the anvil 118 is slid to the forward position, the retraction switch 330 may be actuated such that the retraction cam 202 is driven to rotate in rotation direction 683. The lobes 209 of the retraction cam 202 impact the cleat 235 of the retractor 208, driving the anvil 118 in direction 225 proximally toward the impaction cam 114. An implement may receive the retraction force transferred through the handle 106, thus driving the implement toward extraction. In some cases, when an implement is successfully retracted, the anvil 118 is driven in direction 225 proximally toward the impaction cam 114 such that the limit bar 332 is disengaged from the limit lever 331, thus de-actuating the retraction switch 330 and automatically ceasing the retraction process. Although a lever arm limit switch is shown and described other limit switch and sensor types are contemplated herein. For example, other limit switches and sensors may be inductive proximity switches, capacitive proximity switches, photoelectric switches, reed switches, hall effect sensors, etc.

The motors described herein may be brush or brushless. Brush motors have brushes which are used to commutate the motor to cause it to spin. The armature of a brush motor has a commutator or brush that allows electricity to flow into the armature. The armature is energized with an electro-magnetic field which may cause the armature to spin. A brushless motor is controlled electronically and by definition does not have any brushes. An embodiment may include a brushless motor because it is longer lasting, more energy efficient, has more power per unit volume, and is potentially sterilizable. The motor 108 can be reversed in several ways. One way to reverse the motor 108, is to reverse the current to a brush motor 108 by employing a double pole double throw switch or a switch with relays or transistor circuit. Motor controls, for either brush or brushless motors, known in the art may be used in the impactor embodiments described herein. FIG. 10A illustrates an embodiment of an impactor 100 with a mode selector input 600. The mode selector input 600 may be pressed in direction 602 (opposite direction 604) to place the impactor 100 in a first mode, for example, an impaction mode. The mode selector input 600 may be pressed in direction 604 (opposite direction 602) to place the impactor 100 in a second mode, for example, a retraction mode.

The mechanical resistance of the embodiments described herein is such that it doesn't overcome the stall torque of the motor 108 (shown in FIG. 1B). In some embodiments, a motor with about 12,000 revolutions per minute (RPM) and a gear ratio of at least 10 to 1 may be used. Motor 108 speeds can also vary from about 6,000 RPM to about 8,000 RPM; about 8,000 RPM to about 10,000 RPM; about 10,000 RPM to about 12,500 RPM; or about 12,500 RPM to about 15,000 RPM and beyond. Gear ratios can also be about 5:1 to 10:1; about 10:1 to 15:1; about 15:1 to 20:1; etc. Through experimentation with an embodiment, it was found that a motor with 18,600 RPM and sufficient stall and running torque may be advantageous for embodiments herein. Higher RPMs and somewhat lower speeds may also work. For example, speeds of about 12,000 RPM to about 25,000 RPM may also be suitable. In a particular embodiment, the motor has about 18,600 RPM and the gear train has an about 10 to 1 reduction ratio, putting the impact frequency at a calculated 30 Hz. The actual impact frequency is less, due to frictional losses. At full speed (about 18,600 RPM), the frequency may be about 20 Hz to about 23 Hz (i.e., impacts per second).

Various studies have shown that excessive noise in the surgical operating theater contributes to hearing loss, increased stress, loss of focus, and reduced quality of teamwork. National Institute for Occupational Safety and Health (NIOSH) has established a guideline for workplace noise safety. In this guideline, the noise levels may be less than 85 dBA over an 8 hour period. Further, the allowable noise exposure time limit decreases by half for every 3 dBA increase in loudness. This equates to 15 minutes of exposure for 100 dBA and 3.7 minutes for 106 dBA. The World Health Organization (WHO) has established an Operating Theatre noise guideline as well. The WHO states that the noise must not increase 30 DBA beyond whispering inaudibly in a library. Roughly this is around 60 dBA. Impactor embodiments, described herein, can exceed a sound level of about 100 dBA to about 105 dBA, however, use of the impactor may not exceed about 3 minutes. The noise may be created by the cam lobe 115 striking the anvil 118. The difficulty with sound mediation is finding sound absorption materials that are sterilizable. Conventional sound absorption materials are thermoplastic polymers that have softening or melting temperatures below sterilization temperatures. Employing a disposable boot that can be ETO (Ethylene Oxide Sterilization) sterilized, or radiation sterilized, is another approach to sound absorption. The "boot" can also serve several purposes including eliminating sterilization of impactor embodiments and providing a way to attach sound absorption materials.

Figure 11:
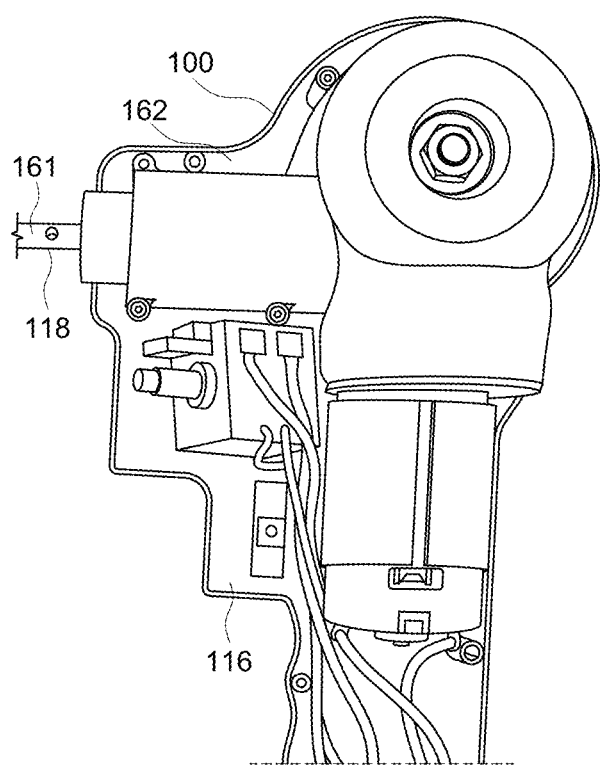
FIG. 11 illustrates an embodiment of a noise reduction mechanism.

FIG. 11 illustrates an embodiment including one or more noise reduction mechanisms. By experiment, it has been shown that some embodiments of the impactor 100 have a noise level of above about 100 dB on the A and C scales. Much of the noise is generated by the drive train but primarily by the anvil 118 engaging the cam lobe 140. The cam housing 116 reduces the noise, at least partially. As described above, the recommended NIOSH noise exposure limit is 85 dB. Several solutions for reducing noise, for example below 85 dB are contemplated herein. For example, vapor deposition of a coating 161, for example, carbon, ceramic, and/or high temperature polymer coating (e.g., Teflon) on the anvil 118 may be used to reduce or eliminate the metal-to-metal sound during impaction. Another example of sound damping may be to apply a coat 162 to an inside of the cam housing 116 and/or housing 102 with a meta-metal substrate, a graphene infused material, or another sound damping material. Another possible material may be stainless steel foam formed by sintering stainless steel powder with salt crystals and removing the salt crystals to form the foam. For example, sinter stainless foam may be used to coat the inside of the cam housing 116 and/or housing 102. A subsequent coat in the inside of the cam housing 116 and/or housing 102 may be a thin foamed polyurethane. The above approaches, or combinations thereof, are envisioned to either capture the sound waves or reflect them so that they are inert.

Figure 14:
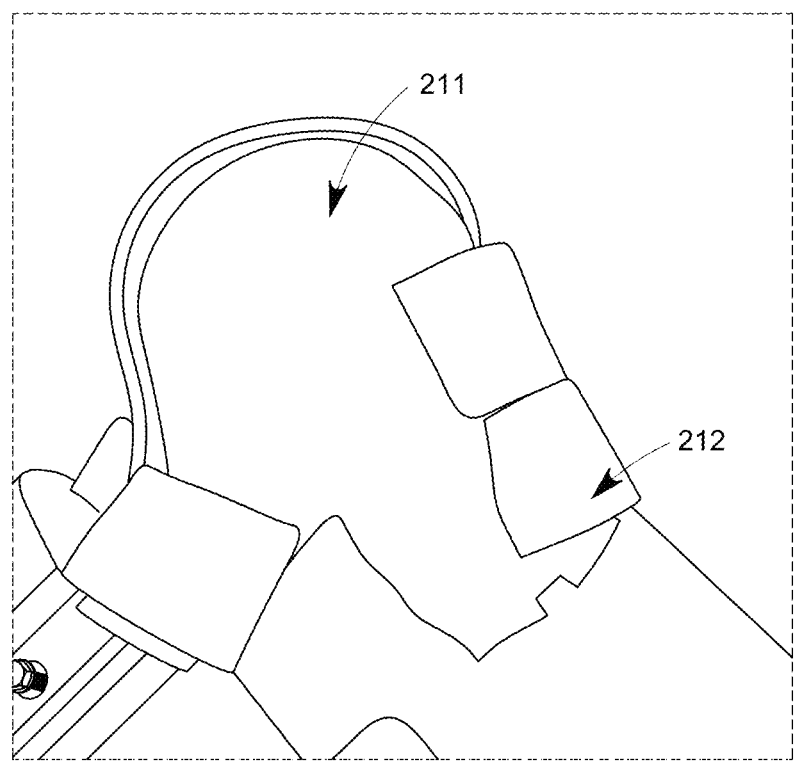
FIG. 14 illustrates sound absorbing material coupled to an embodiment of an impaction device.

FIG. 14 shows one or more layers 211 of a sound absorbing media (e.g., one or more layers of SonoLayr) attached to a boot 212 (e.g., thermoplastic urethane, thermoset urethane, etc.). The one or more layers 211 of media may be electrospun although other thin electrospun and/or acoustical absorbing materials can be employed.

Figure 15:
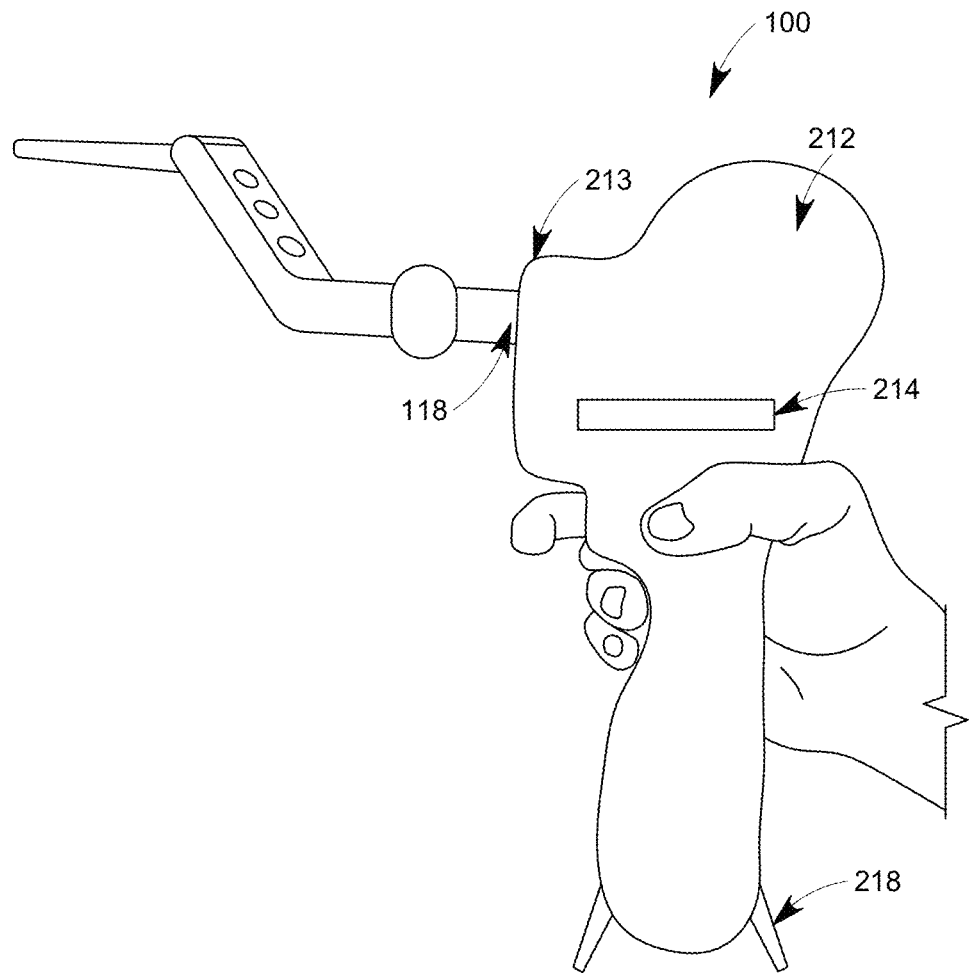
FIG. 15 illustrates a boot coupled to an embodiment of an impaction device.

FIG. 15 shows an embodiment with a boot 212 that may be removably coupled to an impactor 100. The boot 212 can be made of soft urethane, silicone, or the like. Alternatively, or additionally, the boot 212 can be made of thermoplastic materials such as polyethylene, polypropylene, and thermoplastic rubber. The boot 212 can be designed to attach to an implement 213 that snaps onto the impactor anvil 118. The other end of the implement 213 can incorporate a connection mechanism similar to the connection mechanism 105 described elsewhere herein. The boot 212 could be disposable. The boot 212 may be designed with one or more pleats 214 that facilitate sterile fitting or dressing of the boot 212 over the L shaped form of the impactor. The boot 212 could fit over the impactor 100 and be tied securely at the open end. The boot 212 could be sufficiently large enough to maintain sterility as it is fitted over the impactor 100. Pull tabs 218, extruded from the boot 212, also serve as a way to maintain sterile technique because the pull tabs 218 may keep a user's hands away from the impactor 100 during removal and installation of the boot 212.

The anvil 118 and/or the one or more cam lobes 140 may be coated with a sound deadening material such as a PEEK (polyetheretherketone) film. It has been found that coating the anvil 118 and the cam lobes 115 may achieve approximately 3 dBA sound reduction.

Glass microbubbles ranging in size from about 5 microns to about 100 microns can be mixed in a ratio of about 15% to about 75% with the boot 212 material, for example, urethane, silicone, or the like. The glass microbubbles serve to trap the sound, then bounce and dissipate inside the microbubbles. Another sound damping approach may be to keep an air void between one or more sound damping layers (e.g., SonoLayr) and boot 212. The air between layers of media facilitates sound damping by allowing the sound waves to bounce back and forth. This can be accomplished with dots of hot melt polyethylene or polypropylene dots between sound damping layers and the boot material. Maintaining an air gap between materials can also be accomplished with other materials and methods such as plastic netting and by molding/forming ridges or dots 219 on the inside of the boot or impactor housing 220. Other materials can be employed for sound damping.

One experiment demonstrated that with a combination of two layers of SonoLayr and Sorbithane, a weighted urethane material, an 8 dBA reduction in sound was achieved.

Another experiment utilized a combination of two layers of SonoLayr and a coating of 50% glass microbubble/40 shore A urethane mixture, an about 10 dBA to an about 12 dBA sound reduction was achieved.

As a further improvement, a high temperature (e.g., above 350 degrees Fahrenheit) silicone, thermoset, or thermoplastic can be loaded with glass microbubbles 215 in a ratio of about 5% to about 50%. This mixture can be applied as a liner or over molding to the inside of the housings 102 (shown in FIGS. 1A and 1B). Based on experimentation, the sound leakage occurs through the spaces around the control input 103, in the battery compartment 223, and the anvil 118 area of the housing 102. These areas may be sufficiently plugged with sound reduction material. For example, sound damping materials, or combinations thereof, may be arranged with, positioned with, and/or coupled to the tolerances between elements of the impactor, for example, the control input 103, in the battery compartment, and/or the anvil 118 area of the housing 102.

Further, increased sound damping may be achieved, for example, greater than about 10 dBA to about 12 dBA sound reduction. Increased sound damping can be accomplished by wrapping the cam housing 116 (shown in FIG. 11) with high temperature silicone and installing or over molding a liner to thin stainless, high temperature polycarbonate or polyester housings 102. The sound damping solutions described herein may be used alone or combination.

Previously the use of stainless powder with salt crystals was described as a way to manufacture stainless steel foam. Creating a stainless steel foam can also be accomplished through an MIM (Metal Injection Molding) process, or a PM (Powdered Metal) process. In this process stainless steel powder is mixed with either salt crystals, glass microbubbles, ceramic microbubbles, and/or any other microbubble mixture. In the MIM process, the stainless powder is mixed with resin and microbubbles and/or salt crystals. During the injection molding process, a precursor part is molded with the resin binding the mixture described herein. A secondary sintering process at approximately 2000 degrees Fahrenheit melts and drives off the resin microbubble/salt crystal mixture leaving a pocketed foam. This stainless steel foam can be used for the housings 102 (shown In FIGS. 1A and 1B) and/or the cam housings 116 (shown in FIG. 11). A machining step may be used to establish accurate dimensions for the bosses and standing ribs. The MIM process has varying shrink rates that can reach 20%, thus limiting dimensional accuracy. The stainless steel foam can serve to reduce the weight of the housing(s) and/or be used for sound damping. Although the aforementioned may be a difficult process, there is a processing window that would allow for fabricating these parts.

In yet another approach for the housings 102 the MIM, Powdered Metal, precision die casting and other processes can produce a thin stainless part, for example as little as 0.3 mm (0.017 inch) thickness. Thin stainless parts may be particularly useful in reducing weight and/or combining one or more liners or over molding one or more liners for sound reduction.

Figure 16A:
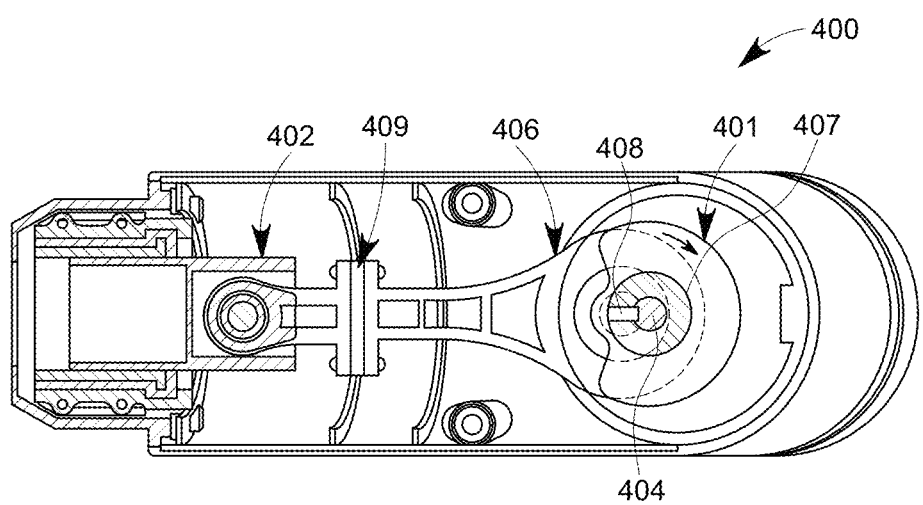
FIGS. 16A-16B illustrate an embodiment of an impaction mechanism of an impaction device.
Figure 16B:
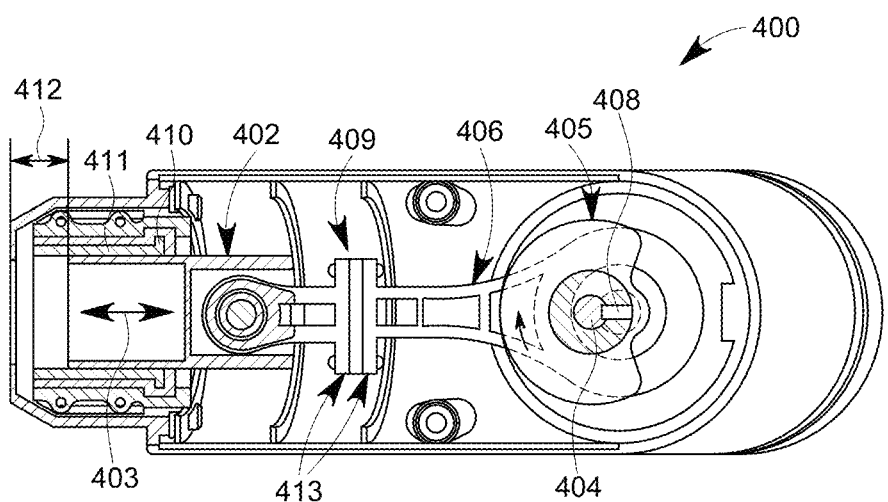

FIGS. 16A and 16B show another approach to an automatic impactor 400 with a modified eccentric-cam linear actuator 401. Several massaging systems known in the art employ a similar approach but are not useful for orthopedic surgery. Muscles and tendons, as intended, absorb the back force of a massager. However, the back force in a massager style impactor can stress a surgeon's hand, wrist, and shoulder in orthopedic implant surgery. The back force may be mitigated in a surgical orthopedic impactor. Mitigating back force may be useful to the orthopedic surgeon.

Conventional systems employ linear actuator systems for orthopedic surgery. However, linear actuator systems can be cumbersome and difficult to use. For example, these linear actuator systems may be excessively heavy, unreliable, and inherently create a large unmitigated back force. Additionally, linear actuator systems may also have large part counts that negatively affect product reliability. The weight of these systems is typically unbalanced and as result, stresses a surgeon's wrist and shoulder. The unbalanced weight can cause the surgeon to grip harder, further exacerbating the stress on the surgeon's wrist and shoulder. This stress becomes more acute with older surgeons.

FIGS. 16A and 16B shows an automatic impactor 400 in which the working mechanism may be positioned directly over a surgeon's gripped hand (not shown). In this mechanism, the anvil 402 is in a return state 403. Further, FIG. 16B shows the anvil 402 in a forward state. The anvil 402 slides in a bushing 411 for a defined distance of 412. The defined distance 412 is determined by the length of a stroke of the linear crank 406. A motor, not shown, has a shaft 404 that is connected to a coupling 407 (shown in FIG. 16A). The coupling 407 is operatively coupled to an eccentric cam 405 and a linear crank 406. The linear crank 406 incorporates two platens 413 that sandwich a force mitigating buffer 409. The force mitigating buffer 409 can have a slight preload to reduce the backlash, lash, or play in the mechanism. The force mitigating buffer 409 can be made of high Shore A (60 to 100) high temperature urethane, silicone, or a stainless conical spring and the like. It can be made of two or more layers in which a softer layer (30 to 50 Shore A) and a harder layer, as described above, create an increasing resistance as compression is increased. The compressibility of the force mitigating buffer 409 may absorb energy to uniformly reduce the back force. This force mitigating buffer 409 can also reduce the impact force, however, by employing a BLDC (brushless DC electric motor) motor, which is inherently more powerful, the loss of impact force can be offset once the force mitigating buffer 409 is compressed.

Figure 17:
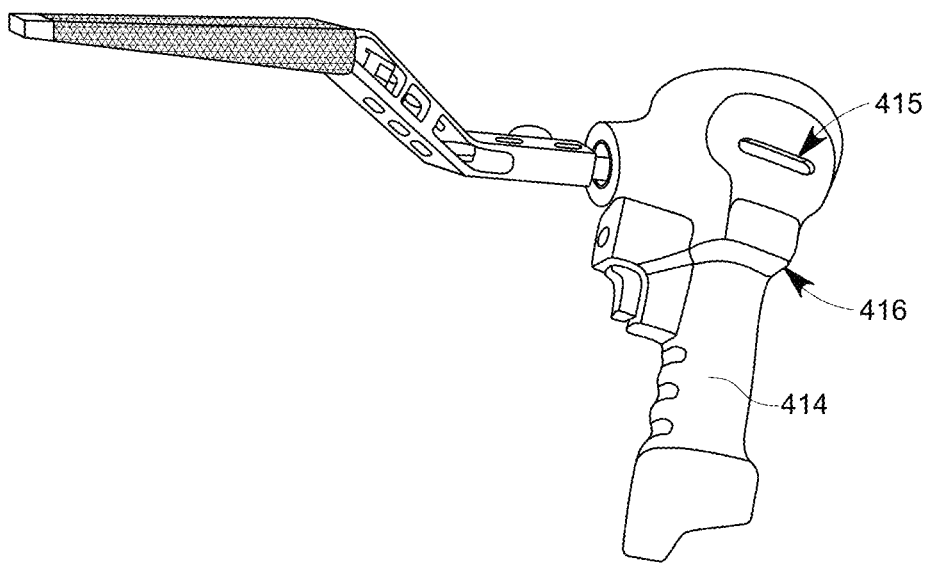
FIG. 17 illustrates an embodiment of an impaction device with a gasket for back force mitigation.

FIG. 17 shows another embodiment of a mechanism to mitigate back force. In this embodiment, the handle 414 is isolated from the body of the impactor 415 with a high temperature gasket 416. The high temperature gasket 416 can absorb the vibrations and back force. The gasket 416 can be fabricated with high temperature silicone, urethane, or any high temperature elastomer. Thermoplastic elastomers can also be employed as a sterile disposable (i.e., single use). Coupled with the urethane or thermoplastic elastomer boot 212 described elsewhere herein, the gasket 416 can offer further back force isolation by allowing limited, independent movement of the impactor 415 with respect to the handle 414.

The impaction mechanisms described herein are capable of achieving high frequency impacts. High frequency is described herein as about 10 Hz to about 35 Hz; about 15 Hz to about 30 Hz; about 20 Hz to about 25 Hz; etc. The term low impact force used herein is a relative term and should be understood to mean about 330 N (75 lbs. of force) to about 890 N (200 lbs. of force); about 440 N (100 lbs. of force) to about 800 N (180 lbs. of force); about 550 N (125 lbs. of force) to about 775 N (175 lbs. of force); etc.

An experiment was performed to compare the performance of a mallet versus an impactor producing a lower impact force at a higher frequency. The test involved broaching a medium-sized femur to expand its canal for implant insertion using a progressive series of broaches, beginning with a starter broach and incrementally increasing from sizes #6 to #10, with the final broach being a #10. Measurements were taken with a Mitutoyo Absolute Digimatic Vernier Caliper, calibrated and traceable to the National Bureau of Standards, ensuring high precision. Measurements recorded the distance from the top of the cortical rim to the top of the broach at each step. The objective was to compare insertion equivalency between an automatic impactor and a 2-pound manual mallet. During testing, the mallet applied an impact force of 1.2 kN (282 lbs. of force) to 1.4 kN (311 lbs. of force) at a frequency of up to about 2 Hz, whereas the automatic impactor delivered a peak force of 0.75 kN (167 lbs. of force) at about 23 Hz. For the #10 broach, the automatic impactor achieved final insertion at a reading of 11.38 mm to 11.39 mm from an initial position of 18.15 mm. In comparison, the manual mallet achieved final insertion at 11.25 mm to 11.27 mm from an initial position of 18.25 mm. These results demonstrate relative insertion equivalency between the two methods, despite the difference in impact forces, confirming that the automatic impactor can achieve similar final insertion depths as a manual mallet, providing a reliable alternative for femoral broaching.

EXAMPLES

Example 1. An orthopedic impactor system, comprising: a motor operatively coupled to a driveshaft, wherein the driveshaft is configured to be driven in a first direction and a second direction; an anvil configured to be operatively coupled to an implement handle; and an impaction cam operatively coupled to the driveshaft, wherein: the impaction cam is configured to strike the anvil when driven by the driveshaft to drive the anvil in an impaction direction, impaction cam is configured to be retarded when a minimum force is sustained by the anvil, and retarding the impaction cam is configured to force the impaction cam out of contact with the anvil in a first axial direction along a longitudinal axis of the driveshaft.

Example 2. The orthopedic impactor system of example 1, further comprising a spring configured to force the impaction cam in a second axial direction along the longitudinal axis of the driveshaft into contact with the anvil.

Example 3. The orthopedic impactor system of any one of the preceding examples, but particularly example 1, wherein the impaction cam is operatively coupled to the driveshaft via a plurality of ball bearings interfacing with a plurality of respective spherical grooves defined by the driveshaft and a plurality of respective sockets defined by the impaction cam.

Example 4. The orthopedic impactor system of any one of the preceding examples, but particularly example 1, further comprising a speed control input configured to place the impactor in a first mode or second mode.

Example 5. The orthopedic impactor system of any one of the preceding examples, but particularly example 1, further comprising a battery electrically coupled to the motor.

Example 6. The orthopedic impactor system of any one of the preceding examples, but particularly example 1, wherein the anvil is coupled to the implement using a connection mechanism.

Example 7. The orthopedic impactor system of any one of the preceding examples, but particularly example 6, wherein the connection mechanism includes a plurality of lockable positions with respect to a longitudinal axis of the anvil.

Example 8. The orthopedic impactor system of any one of the preceding examples, but particularly example 1, further comprising a vibratory assembly coupled to the implement handle.

Example 9. The orthopedic impactor system of any one of the preceding examples, but particularly example 1, wherein the system is configured to produce high-frequency, low force impacts.

Example 10. The orthopedic impactor system of any one of the preceding examples, but particularly example 1, further comprising one or more lights configured to illuminate a working space.

Example 11. The orthopedic impactor system of any one of the preceding examples, but particularly example 1, further comprising a camera configured to record a working space.

Example 12. An orthopedic impactor system, comprising: a motor operatively coupled to a driveshaft, wherein the driveshaft is configured to be driven in a first direction in a first mode for impaction and a second direction in a second mode for retraction; an anvil configured to be operatively coupled to an implement handle; an impaction cam operatively coupled to the driveshaft, wherein: the impaction cam, when in an impaction position, is configured to strike the anvil when driven by the driveshaft in the first direction to drive the anvil in an impaction direction, the impaction cam is configured to be retarded when a minimum force is sustained by the anvil, when retarded, the impaction cam is configured to be forced out of contact with the anvil in a first axial direction along a longitudinal axis of the driveshaft, and the impaction cam is configured to be forced back into the impaction position in a second axial direction when the impaction cam rotates past the anvil; a retraction cam operatively coupled the driveshaft, wherein the retraction cam is configured to be driven to spin by the driveshaft in the second direction; and a retractor configured to be driven by the retraction cam in the second direction, wherein the retractor is configured to strike the anvil to drive the anvil in a retraction direction.

Example 13. The orthopedic impactor system of example 12, further comprising a spring configured to force the impaction cam in a second axial direction along the longitudinal axis of the driveshaft into contact with the anvil.

Example 14. The orthopedic impactor system of any one of the preceding examples, but particularly example 12, wherein the impaction cam is operatively coupled to the driveshaft via a plurality of ball bearings interfacing with a plurality of respective spherical grooves defined by the driveshaft and a plurality of respective sockets defined by the impaction cam.

Example 15. The orthopedic impactor system of any one of the preceding examples, but particularly example 12, further comprising a speed control input configured to adjust a frequency of impacts.

Example 16. The orthopedic impactor system of any one of the preceding examples, but particularly example 12, further comprising a mode selector input configured to place the impactor in a first mode or second mode.

Example 17. The orthopedic impactor system of any one of the preceding examples, but particularly example 12, further comprising a battery electrically coupled to the motor.

Example 18. The orthopedic impactor system of any one of the preceding examples, but particularly example 12, wherein the anvil is coupled to the implement using a connection mechanism.

Example 19. The orthopedic impactor system of any one of the preceding examples, but particularly example 18, wherein the connection mechanism includes a plurality of lockable positions with respect to a longitudinal axis of the anvil.

Example 20. The orthopedic impactor system of any one of the preceding examples, but particularly example 12, further comprising a vibratory assembly coupled to the implement handle.

Example 21. The orthopedic impactor system of any one of the preceding examples, but particularly example 12, wherein the system is configured to produce high-frequency, low force impacts.

Example 22. The orthopedic impactor system of any one of the preceding examples, but particularly example 12, further comprising a light configured to illuminate a working space.

Example 23. The orthopedic impactor system of any one of the preceding examples, but particularly example 12, further comprising a camera configured to record a working space.

Example 24. A method of using an impactor on a prepared bone comprising: activating an impactor for impaction using high-frequency, low force impacts, wherein impaction includes: driving a driveshaft in a first direction to drive an impaction cam operatively coupled to the driveshaft, impacting an anvil with the impaction cam such that the anvil is driven in an impaction direction, when a minimum force is sustained by the anvil, disengaging the impaction cam from the anvil by allowing retardation of the impaction cam with respect to the driveshaft and translating the impaction cam in a second axial direction along a longitudinal axis of the driveshaft until the impaction cam is out of contact with the anvil, and forcing the impaction cam back in a first axial direction to an impaction position for a subsequent impact; broaching a canal of the bone; and installing a stem.

Example 25. The method of example 24, further comprising activating the impactor for retraction, including: driving the driveshaft in a second direction to drive a retraction cam, and impacting a retractor via the retraction cam such that the retractor drives the anvil in a retraction direction.

Example 26. The method of any one of the preceding examples, but particularly example 24, further comprising preparing a canal.

Example 27. A method of using an impactor on a prepared bone comprising: activating an impactor for impaction using high-frequency, low force impacts, wherein impaction includes: driving a driveshaft in a first direction to drive an impaction cam operatively coupled to the driveshaft, impacting an anvil with the impaction cam such that the anvil is driven in an impaction direction, when a minimum force is sustained by the anvil, disengaging the impaction cam from the anvil by allowing retardation of the impaction cam with respect to the driveshaft and translating the impaction cam in a second axial direction along a longitudinal axis of the driveshaft until the impaction cam is out of contact with the anvil, and forcing the impaction cam back in a first axial direction to an impaction position for a subsequent impact; and installing an implement.

Example 28. The method of example 27, further comprising activating the impactor for retraction, including: driving the driveshaft in a second direction to drive a retraction cam, and impacting a retractor via the retraction cam such that the retractor drives the anvil in a retraction direction to remove the implement.

References in the specification to "one embodiment," "an embodiment" "an illustrative embodiment," "some embodiments," etc., indicate that the embodiment described may include a particular feature, structure, or characteristic, but every embodiment may or may not necessarily include that particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to effect such feature, structure, or characteristic in connection with other embodiments whether or not explicitly described.[0048] As used in the description and claims, the singular form "a", "an" and "the" include both singular and plural references unless the context clearly dictates otherwise. At times, the claims and disclosure may include terms such as "a plurality," "one or more," or "at least one;" however, the absence of such terms is not intended to mean, and should not be interpreted to mean, that a plurality is not conceived.

The term "about" or "approximately," when used before a numerical designation or range (e.g., to define a length or pressure), indicates approximations which may vary by (+) or (−) 5%, 1% or 0.1%. All numerical ranges provided herein are inclusive of the stated start and end numbers. The term "substantially" indicates mostly (i.e., greater than 50%) or essentially all of a device, substance, or composition.

As used herein, the term "comprising" or "comprises" is intended to mean that the devices, systems, and methods include the recited elements, and may additionally include any other elements. "Consisting essentially of" shall mean that the devices, systems, and methods include the recited elements and exclude other elements of essential significance to the combination for the stated purpose. Thus, a system or method consisting essentially of the elements as defined herein would not exclude other materials, features, or steps that do not materially affect the basic and novel characteristic(s) of the claimed disclosure. "Consisting of" shall mean that the devices, systems, and methods include the recited elements and exclude anything more than a trivial or inconsequential element or step. Embodiments defined by each of these transitional terms are within the scope of this disclosure.

The examples and illustrations included herein show, by way of illustration and not of limitation, specific embodiments in which the subject matter may be practiced. Other embodiments may be utilized and derived therefrom, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is in fact disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. An orthopedic impactor, comprising:
a motor operatively coupled to a driveshaft, wherein the driveshaft is configured to be driven in a first direction in a first mode for impaction and a second direction in a second mode for retraction;
an anvil configured to be operatively coupled to an implement handle;
an impaction cam operatively coupled to the driveshaft, wherein:
the impaction cam, when in an impaction position, is configured to strike the anvil when driven by the driveshaft in the first direction to drive the anvil in an impaction direction,
the impaction cam is configured to be retarded when a minimum force is sustained by the anvil, when retarded, the impaction cam is configured to be forced out of contact with the anvil in a first axial direction along a longitudinal axis of the driveshaft, and
the impaction cam is configured to be forced back into the impaction position in a second axial direction when the impaction cam rotates past the anvil, wherein the impaction direction is in a radial direction to the first axial direction and the second axial direction;
a retraction cam operatively coupled the driveshaft, wherein the retraction cam is configured to be driven to spin by the driveshaft in the second direction; and
a retractor configured to be driven by the retraction cam in the second direction, wherein the retractor is configured to strike the anvil to drive the anvil in a retraction direction.

2. The orthopedic impactor of claim 1, further comprising a spring configured to force the impaction cam in a second axial direction along the longitudinal axis of the driveshaft into contact with the anvil.

3. The orthopedic impactor of claim 1, wherein the impaction cam is operatively coupled to the driveshaft via a plurality of ball bearings interfacing with a plurality of respective spherical grooves defined by the driveshaft and a plurality of respective sockets defined by the impaction cam.

4. The orthopedic impactor of claim 1, further comprising a speed control input configured to adjust a frequency of impacts.

5. The orthopedic impactor of claim 4, further comprising a mode selector input configured to place the impactor in a first mode or second mode.

6. The orthopedic impactor of claim 1, further comprising a battery electrically coupled to the motor.

7. The orthopedic impactor of claim 1, wherein the anvil is coupled to the implement handle using a connection mechanism.

8. The orthopedic impactor of claim 7, wherein the connection mechanism includes a plurality of lockable positions with respect to a longitudinal axis of the anvil.

9. The orthopedic impactor of claim 1, further comprising a vibratory assembly coupled to the implement handle.

10. The orthopedic impactor of claim 1, wherein the impactor is configured to produce high-frequency, low force impacts.

11. An orthopedic impactor, comprising:
a motor operatively coupled to a driveshaft, wherein the driveshaft is configured to be driven in a first direction and a second direction;
an anvil configured to be operatively coupled to an implement handle; and
an impaction cam operatively coupled to the driveshaft, wherein:
the impaction cam, when in an impaction position, is configured to strike the anvil when driven by the driveshaft in the first direction to drive the anvil in an impaction direction,
the impaction cam is configured to be retarded when a minimum force is sustained by the anvil,
the impaction cam is configured to be forced back into the impaction position in a second axial direction when the impaction cam rotates past the anvil, and
retarding the impaction cam is configured to force the impaction cam out of contact with the anvil in a first axial direction along a longitudinal axis of the driveshaft, wherein the impaction direction is in a radial direction to the first axial direction.

12. The orthopedic impactor of claim 11, further comprising a spring configured to force the impaction cam in a second axial direction along the longitudinal axis of the driveshaft into contact with the anvil.

13. The orthopedic impactor of claim 11, wherein the impaction cam is operatively coupled to the driveshaft via a plurality of ball bearings interfacing with a plurality of respective spherical grooves defined by the driveshaft and a plurality of respective sockets defined by the impaction cam.

14. The orthopedic impactor of claim 11, further comprising a speed control input configured to place the impactor in a first mode or second mode.

15. The orthopedic impactor of claim 11, further comprising a battery electrically coupled to the motor.

16. The orthopedic impactor of claim 11, wherein the anvil is coupled to the implement handle using a connection mechanism.

17. The orthopedic impactor of claim 16, wherein the connection mechanism includes a plurality of lockable positions with respect to a longitudinal axis of the anvil.

18. The orthopedic impactor of claim 11, further comprising a vibratory assembly coupled to the implement handle.

19. The orthopedic impactor of claim 11, wherein the system impactor is configured to produce high-frequency, low force impacts.

20. An orthopedic impactor, comprising:
- a motor operatively coupled to a driveshaft, wherein the driveshaft is configured to be driven in a first direction in a first mode for impaction and a second direction in a second mode for retraction;
- an anvil configured to be operatively coupled to an implement handle;
- an impaction cam operatively coupled to the driveshaft, wherein:
  the impaction cam, when in an impaction position, is configured to strike the anvil when driven by the driveshaft in the first direction to drive the anvil in an impaction direction,
  the impaction cam is configured to be retarded when a minimum force is sustained by the anvil, when retarded, the impaction cam is configured to be forced out of contact with the anvil in a first axial direction along a longitudinal axis of the driveshaft, and
  the impaction cam is configured to be forced back into the impaction position in a second axial direction when the impaction cam rotates past the anvil;
  the impaction cam including a plurality of sockets to interface with the driveshaft;
- a retraction cam operatively coupled the driveshaft, wherein the retraction cam is configured to be driven to spin by the driveshaft in the second direction; and
- a retractor configured to be driven by the retraction cam in the second direction, wherein the retractor is configured to strike the anvil to drive the anvil in a retraction direction.

* * * * *